(12) United States Patent
Schalk

(10) Patent No.: US 10,253,335 B2
(45) Date of Patent: *Apr. 9, 2019

(54) METHOD FOR PRODUCING BETA-SANTALENE

(71) Applicant: Firmenich SA, Geneva (CH)

(72) Inventor: Michel Schalk, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/688,956

(22) Filed: Aug. 29, 2017

(65) Prior Publication Data

US 2018/0105837 A1    Apr. 19, 2018

Related U.S. Application Data

(60) Division of application No. 14/530,651, filed on Oct. 31, 2014, now Pat. No. 9,777,293, which is a continuation of application No. 13/124,866, filed as application No. PCT/IB2009/055589 on Dec. 9, 2009, now Pat. No. 8,877,461.

(30) Foreign Application Priority Data

Dec. 11, 2008 (EP) ..................... 08171298
Aug. 17, 2009 (WO) ............... PCT/IB2009/053623

(51) Int. Cl.
    *C12P 21/06*    (2006.01)
    *C12P 5/00*     (2006.01)
    *C12N 9/88*     (2006.01)

(52) U.S. Cl.
    CPC ............... *C12P 5/002* (2013.01); *C12N 9/88* (2013.01); *C12P 5/007* (2013.01); *C12Y 402/03083* (2013.01)

(58) Field of Classification Search
    None
    See application file for complete search history.

(56) References Cited

U.S. PATENT DOCUMENTS

2008/0268500 A1    10/2008    Schalk

FOREIGN PATENT DOCUMENTS

| WO | WO 2006/134523 A2 | 12/2006 |
| WO | WO2009109597 A1 | 9/2009 |
| WO | WO 2010 067309 A1 | 6/2010 |
| WO | WO 2011 00026 A1 | 1/2011 |

OTHER PUBLICATIONS

Emanuelsson et al., "ChloroP, a neural network based method for predicting chloroplast transit peptides and their cleavage sites," Protein Science, 8:978-984 (1999).
Gamborg, "Nutrient Requirements of Suspension Cultures of Soybean Root Cells," Experimental Cell Research, 50:151-158 (1968).
Hernandez et al., "De novo bacterial genome sequencing: Millions of very short reads assembled on a desktop computer," Genome Research, 18:802-809 (2008).
Huang, "A Contig Assembly Program Based on Sensitive Detection of Fragment Overlaps," Genomics, 14:18-25 (1992).
Jones et al., "Quantitative co-occurrence of sesquiterpenes; a tool for elucidating their biosynthesis in Indian sandalwood, *Santalum album*," Phytochemistry, 67:2463-2468(2006).
Jones et al., "Isolation of cDNAs and functional characterization of two multi-product terpene synthase enzymes from sandalwood . . . ," Arch Biochem. Biophys. 477:121-130 (2008).
Lefort et al.,"An efficient micro-method of DNA isolation from mature leaves of four hardwood tree species *acer, fraxinus, prunus* and *quercus*," Ann. For. Sci., 56:259-263(1999).
Li et al., "Mapping short DNA sequencing reads and calling variants using mapping quality scores," Genome Research, 18(11):1851-1858 (2008).
Martin et al., "Engineering a mevalonate pathway in *Escherichia coli* for production of terpenoids," Nature Biotechnology, 21(7):796-802 (2003).
Murashige et al, "A Revised Medium for Rapid Growth and Bio Assays with Tobacco Tissue Cultures," Physiologia Plantarum, 15(3):473-497 (1962).
Saito et al.,"Diastereo- and Enantio-Controlled Synthesis of Sandalwood Constituents (−)-β-Santalene and (+)-Epi-β-santalene . . . ," Tetrahedron Letters, 36(49):9003-9006(1995).
Schardl et al., "Design and construction of a versatile system for the expression of foreign genes in plants," Gene, 61(1):1-11 (1987).
Stemmer et al., "DNA shuffling by random fragmentation and reassembly: In vitro recombination for molecular evolution," Proc. Natl. Acad. Sci. USA, 91:10747-10751 (1994).
Takahashi et al, "Metabolic Engineering of Sesquiterpene Metabolism in Yeast," Biotechnol. Bioeng., 97:170-181 (2007).
Tatusova et al., "BLAST 2 Sequences, a new tool for comparing protein and nucleotide sequences," FEMS Microbiology Letters, 174:247-250 (1999).
Wu et al., "Redirection of cytosolic or plastidic isoprenoid precursors elevates terpene production in plants," Nature Biotechnology, 24(11):1441-1447 (2006).
Zerbino et al., "Velvet: Algorithms for de novo short read assembly using de Bruijn graphs," Genome Research, 18:821-829 (2008).
Jones, C.G. et al, Monoterpene synthase [Santalum album]., NCBI GenBank Accession No. ACF24767, Sep. 2, 2008.

(Continued)

*Primary Examiner* — Jennifer E Graser

(57) ABSTRACT

The present invention provides a method of producing β-santalene, said method comprising contacting at least one polypeptide with farnesyl pyrophosphate (FPP). In particular, said method may be carried out in vitro or in vivo to produce β-santalene, a very useful compound in the fields of perfumery and flavoring. The present invention also provides the amino acid sequence of a polypeptide useful in the method of the invention. A nucleic acid encoding the polypeptide of the invention and an expression vector containing said nucleic acid are also part of the present invention. A non-human host organism or a cell transformed to be used in the method of producing β-santalene is also an object of the present invention.

19 Claims, 5 Drawing Sheets

Specification includes a Sequence Listing.

(56) References Cited

OTHER PUBLICATIONS

Rocci,L. et al, Santalene bergamotene synthase 1 [Santalum album]. ,NCBI GenBank Accession No. ADP30866, Nov. 6, 2010.
Jones et al (J. Biol. Chem. 286 (20), 17445-17454 (2011).
Jones et al (Arch Biochem. Biophys. Sep. 2008. 477:122-130).
Mikayama et al. (Nov. 1993, Proc.Natl.Acad.Sci. USA, vol. 90 : 10056-10060).
Rudinger et al. (Jun. 1976. Peptide Hormones. Biol.Council. pp. 5-7).
Chothia et al (The EMBO Journal, 1986, 5/4:823-26).
International Search Report and Written Opinion of the International Searching Authority dated Feb. 15, 2010 for application No. PCT/IB2009/055589 filed Dec. 9, 2009.
Altschul et al., "Basic Local Alignment Search Tool," J. Mol. Biol., 215:403-410 (1990).
Altschul et al., "Amino Acid Substitution Matrices from an Information Theoretic Perspective," J. Mol. Biol., 219:555-565 (1991).
Asadollahi et al., "Production of Plant Sesquiterpenes in S. cerevisiae: Effect of ERG9 Repression on Sesquiterpene Biosynthesis," Biotechnol. Bioeng., 99(3):666-677 (2008).
Dewick, "The biosynthesis of C5—C25 terpenoid compounds," Nat. Prod. Rep., 19:181-222 (2002).

Beta Santalene

Beta Santalol

SEQUENCE LISTING

<160> NUMBER OF SEQ ID NOS: 27

<210> SEQ ID NO 1

```
<211> LENGTH: 548
<212> TYPE: PRT
<213> ORGANISM: Santalum album

<400> SEQUENCE: 1

Met Ala Thr Asp Asn Asp Ser Ser Glu Asn Arg Arg Met Gly Asn Tyr
1               5                   10                  15

Lys Pro Ser Ile Trp Asn Tyr Asp Phe Leu Gln Ser Leu Ala Thr Arg
            20                  25                  30

His Asn Ile Met Glu Glu Arg His Leu Lys Leu Ala Glu Lys Leu Lys
        35                  40                  45

Gly Gln Val Lys Phe Met Phe Gly Ala Pro Met Glu Pro Leu Ala Lys
    50                  55                  60

Leu Glu Leu Val Asp Val Val Gln Arg Leu Gly Leu Asn His Arg Phe
65                  70                  75                  80

Glu Thr Glu Ile Lys Glu Ala Leu Phe Ser Ile Tyr Lys Asp Glu Ser
                85                  90                  95

Asn Gly Trp Trp Phe Gly His Leu His Ala Thr Ser Leu Arg Phe Arg
            100                 105                 110

Leu Leu Arg Gln Cys Gly Leu Phe Ile Pro Gln Asp Val Phe Lys Thr
        115                 120                 125

Phe Gln Ser Lys Thr Gly Glu Phe Asp Met Lys Leu Cys Asp Asn Val
    130                 135                 140

Lys Gly Leu Leu Ser Leu Tyr Glu Ala Ser Phe Leu Gly Trp Arg Asp
145                 150                 155                 160

Glu Asn Ile Leu Asp Glu Ala Lys Ala Phe Ala Thr Lys Tyr Leu Lys
                165                 170                 175

Asn Ala Trp Glu Asn Ile Ser Gln Lys Trp Leu Ala Lys Arg Val Lys
            180                 185                 190

His Ala Leu Ala Leu Pro Leu His Trp Arg Val Pro Arg Ile Glu Ala
        195                 200                 205

Arg Trp Phe Val Glu Ala Tyr Gly Glu Glu Asn Met Asn Pro Thr
    210                 215                 220

Leu Leu Lys Leu Ala Lys Leu Asp Phe Asn Met Val Gln Ser Ile His
225                 230                 235                 240

Gln Lys Glu Ile Gly Glu Leu Ala Arg Trp Trp Val Thr Thr Gly Leu
                245                 250                 255

Asp Lys Leu Ala Phe Ala Arg Asn Asn Leu Leu Gln Ser Tyr Met Trp
            260                 265                 270

Ser Cys Ala Ile Ala Ser Asp Pro Lys Phe Lys Leu Ala Arg Glu Thr
        275                 280                 285

Ile Val Glu Ile Gly Ser Val Leu Thr Val Val Asp Asp Ala Tyr Asp
    290                 295                 300

Val Tyr Gly Ser Met Asp Glu Leu Asp Leu Tyr Thr Asn Ser Val Glu
305                 310                 315                 320

Arg Trp Ser Cys Thr Glu Ile Asp Lys Leu Pro Asn Thr Leu Lys Leu
                325                 330                 335

Ile Phe Met Ala Met Phe Asn Lys Thr Asn Glu Val Gly Leu Arg Val
            340                 345                 350

Gln His Glu Arg Gly Tyr Ser Gly Ile Thr Thr Phe Ile Lys Ala Trp
        355                 360                 365

Val Glu Gln Cys Lys Ser Tyr Gln Lys Glu Ala Arg Trp Tyr His Gly
    370                 375                 380

Gly His Thr Pro Pro Leu Glu Glu Tyr Ser Leu Asn Gly Leu Val Ser
```

```
            385                 390                 395                 400
Ile Gly Phe Pro Leu Leu Ile Thr Gly Tyr Val Ala Ile Ala Glu
                405                 410                 415

Asn Glu Ala Ala Leu Asp Lys Val His Pro Leu Pro Asp Leu Leu His
                420                 425                 430

Tyr Ser Ser Leu Leu Ser Arg Leu Ile Asn Asp Met Gly Thr Ser Ser
                435                 440                 445

Asp Glu Leu Glu Arg Gly Asp Asn Leu Lys Ser Ile Gln Cys Tyr Met
450                 455                 460

Asn Gln Thr Gly Ala Ser Glu Lys Val Ala Arg Glu His Ile Lys Gly
465                 470                 475                 480

Ile Ile Glu Glu Asn Trp Lys Ile Leu Asn Glu Cys Cys Phe Asp Gln
                485                 490                 495

Ser Gln Phe Gln Glu Pro Phe Val Thr Phe Asn Leu Asn Ser Val Arg
                500                 505                 510

Gly Ser His Phe Phe Tyr Glu Phe Gly Asp Gly Phe Gly Val Thr Asn
                515                 520                 525

Ser Trp Thr Lys Val Asp Met Lys Ser Val Leu Ile Asp Pro Ile Pro
530                 535                 540

Leu Asp Glu Glu
545

<210> SEQ ID NO 2
<211> LENGTH: 1650
<212> TYPE: DNA
<213> ORGANISM: Santalum album

<400> SEQUENCE: 2
atggctaccg ataatgacag ctctgaaaac cgtcgtatgg gtaattacaa gccgtccatc      60
tggaactacg acttcctgca gtccctggct acccgccaca atatcatgga gagcgccac      120 ttgaaactgg cggagaaact gaaaggccag gtgaagttta tgtttggtgc ccgatggag      180 ccgctggcca aactggagct ggttgatgtt gttcagcgcc tgggtctgaa tcatcgcttc      240
gagacggaga ttaaggaggc cctgttcagc atctacaagg atgagagcaa cggttggtgg      300
tttggccacc tgcatgccac cagcctgcgt tttcgcctgc tgcgccagtg tggtctgttc      360
attccgcaag acgttttcaa gacgttccaa agcaagaccg gcgagttcga catgaaactg      420
tgcgacaacg tcaagggttt gctgagcctg tacgaggctt cctttctggg ctggcgtgac      480
gaaaatatcc tggacgaagc gaaagctttt gccacgaagt acctgaagaa cgcatgggaa      540
aacattagcc agaagtggct ggcgaaacgc gtgaagcatg cgttggcact gccgttgcac      600
tggcgtgtgc ctcgtattga agcacgctgg tttgttgagg cgtacggcga ggaggaaaat      660
atgaatccga ccttgctgaa gctggctaag ttggatttta acatggtgca atctattcac      720
caaaaggaaa tcggtgaatt ggcacgttgg tgggtcacca ccgtgtctgga caaactggca      780 ttcgcgcgca taatttgct gcaaagctac atgtggagct cgcgcgatcgc atctgacccg      840 aagtttaagc tggctcgcga accatcgtg gagatcggtt ccgtgctgac tgttgtggat      900
gacgcctacg atgtttacgg tagcatggac gaactggact gtataccaa tagcgtggag      960 cgttggagct gtacggaaat cgataagctg ccgaatacgc tgaaactgat tttatggct     1020 atgtttaaca agaccaatga agttggtctg cgtgttcagc acgagcgtgg ttactccggc     1080
atcaccacct tcattaaggc atgggtcgaa cagtgtaaga gctatcaaaa agaagcgcgc     1140
tggtatcatg gtggtcacac gcctccgctg gaagagtact ccttgaatgg cttggtgagc     1200
```

```
attggtttcc cgctgctgct gattaccggc tacgtcgcca ttgccgaaaa cgaagcagcg    1260
ctggacaaag tgcatccgct gccggatctg ctgcactata gctctctgct gagccgcctg    1320
atcaacgaca tgggtacgag cagcgacgag ctggagcgcg gcgataatct gaaaagcatc    1380
caatgctata tgaatcagac cggcgcgagc gagaaggtgg cgcgcgagca catcaagggc    1440
atcattgagg agaattggaa gattctgaac gaatgttgct tcgaccaaag ccaatttcaa    1500
gagccgttcg tgacgttcaa cctgaacagc gttcgtggtt cccatttctt ttacgagttt    1560
ggtgacggtt tcggtgtgac gaatagctgg accaaggttg acatgaagag cgtcctgatt    1620
gatccgattc cactggatga agaataatga                                     1650
```

<210> SEQ ID NO 3
<211> LENGTH: 551
<212> TYPE: PRT
<213> ORGANISM: Artificial sequence
<220> FEATURE:
<223> OTHER INFORMATION: Polypeptide encoded by the optimized sequence
      SCH10-Ctg8201-opt for expression in E. coli.

<400> SEQUENCE: 3

```
Met Ala Thr Leu Lys Thr Asp Thr Asp Ala Ser Glu Asn Arg Arg Met
1               5                   10                  15

Gly Asn Tyr Lys Pro Ser Ile Trp Asn Tyr Asp Phe Leu Gln Ser Leu
            20                  25                  30

Ala Thr His His Asn Ile Val Glu Glu Arg His Leu Lys Leu Ala Glu
        35                  40                  45

Lys Leu Lys Gly Gln Val Lys Phe Met Phe Gly Ala Pro Met Glu Pro
    50                  55                  60

Leu Ala Lys Leu Glu Leu Val Asp Val Val Gln Arg Leu Gly Leu Asn
65                  70                  75                  80

His Leu Phe Glu Thr Glu Ile Lys Glu Ala Leu Phe Ser Ile Tyr Lys
                85                  90                  95

Asp Gly Ser Asn Gly Trp Trp Phe Gly His Leu His Ala Thr Ser Leu
            100                 105                 110

Arg Phe Arg Leu Leu Arg Gln Cys Gly Leu Phe Ile Pro Gln Asp Val
        115                 120                 125

Phe Lys Thr Phe Gln Asn Lys Thr Gly Glu Phe Asp Met Lys Leu Trp
    130                 135                 140

Asp Asn Val Lys Gly Leu Leu Ser Leu Tyr Glu Ala Ser Tyr Leu Gly
145                 150                 155                 160

Trp Lys Gly Glu Asn Ile Leu Asp Glu Ala Lys Ala Phe Thr Thr Lys
                165                 170                 175

Cys Leu Lys Ser Ala Trp Glu Asn Ile Ser Glu Lys Trp Leu Ala Lys
            180                 185                 190

Arg Val Lys His Ala Leu Ala Leu Pro Leu His Trp Arg Val Pro Arg
        195                 200                 205

Ile Glu Ala Arg Trp Phe Ile Glu Val Tyr Glu Gln Glu Ala Asn Met
    210                 215                 220

Asn Pro Thr Leu Leu Lys Leu Ala Lys Leu Asp Phe Asn Met Val Gln
225                 230                 235                 240

Ser Ile His Gln Lys Glu Ile Gly Glu Leu Ala Arg Trp Trp Val Thr
                245                 250                 255

Thr Gly Leu Asp Lys Leu Asp Phe Ala Arg Asn Asn Leu Leu Gln Ser
            260                 265                 270
```

```
Tyr Met Trp Ser Cys Ala Ile Ala Ser Asp Pro Lys Phe Lys Leu Ala
        275                 280                 285
Arg Glu Thr Ile Val Glu Ile Gly Ser Val Leu Thr Val Val Asp Asp
    290                 295                 300
Gly Tyr Asp Val Tyr Gly Ser Met Asp Glu Leu Asp Leu Tyr Thr Ser
305                 310                 315                 320
Ser Val Glu Arg Trp Ser Cys Val Lys Ile Asp Lys Leu Pro Asn Thr
                325                 330                 335
Leu Lys Leu Ile Phe Met Ser Met Phe Asn Lys Thr Asn Glu Val Gly
            340                 345                 350
Leu Arg Val Gln His Glu Arg Gly Tyr Asn Ser Ile Pro Thr Phe Ile
        355                 360                 365
Lys Ala Trp Val Glu Gln Cys Lys Ser Tyr Gln Lys Glu Ala Arg Trp
    370                 375                 380
Phe His Gly Gly His Thr Pro Pro Leu Glu Glu Tyr Ser Leu Asn Gly
385                 390                 395                 400
Leu Val Ser Ile Gly Phe Pro Leu Leu Leu Ile Thr Gly Tyr Val Ala
                405                 410                 415
Ile Ala Glu Asn Glu Ala Ala Leu Asp Lys Val His Pro Leu Pro Asp
            420                 425                 430
Leu Leu His Tyr Ser Ser Leu Leu Ser Arg Leu Ile Asn Asp Ile Gly
        435                 440                 445
Thr Ser Pro Asp Glu Met Ala Arg Gly Asp Asn Leu Lys Ser Ile His
    450                 455                 460
Cys Tyr Met Asn Glu Thr Gly Ala Ser Glu Glu Val Ala Arg Glu His
465                 470                 475                 480
Ile Lys Gly Val Ile Glu Glu Asn Trp Lys Ile Leu Asn Gln Cys Cys
                485                 490                 495
Phe Asp Gln Ser Gln Phe Gln Glu Pro Phe Ile Thr Phe Asn Leu Asn
            500                 505                 510
Ser Val Arg Gly Ser His Phe Tyr Glu Phe Gly Asp Gly Phe Gly
        515                 520                 525
Val Thr Asp Ser Trp Thr Lys Val Asp Met Lys Ser Val Leu Ile Asp
    530                 535                 540
Pro Ile Pro Leu Gly Glu Glu
545                 550

<210> SEQ ID NO 4
<211> LENGTH: 1656
<212> TYPE: DNA
<213> ORGANISM: Artificial sequence
<220> FEATURE:
<223> OTHER INFORMATION: Optimized sequence for expression in E. coli.

<400> SEQUENCE: 4
atggcaacct tgaagactga caccgacgct agcgagaatc gtcgcatggg caactataaa      60
ccgagcattt ggaactacga tttcctgcaa agcctggcta cccaccacaa tatcgtggag     120
gagcgtcacc tgaaactggc agaaaaattg aaaggccaag tgaattcat gttcggcgca     180
ccgatggaac gctggcgaa actggagctg gtcgacgtgg tccaacgcct gggtctgaat     240
cacctgtttg aaaccgaaat taagaggca ctgttcagca tctataagga cggttcgaac     300
ggttggtggt tcggtcacct gcatgcaacc agcctgcgtt ttcgtctgct gcgtcagtgt     360
ggcctgttca ttccgcagga cgtctttaaa acctttcaga acaaaaccgg cgagtttgac     420
atgaagctgt gggacaatgt gaaaggcctg ttgagcctgt atgaggcgag ctacctgggt     480
```

```
tggaagggtg aaaacatcct ggatgaagca aaggcattta ccaccaagtg tctgaagagc      540
gcgtgggaaa atatctctga gaaatggttg gcgaaacgtg tgaagcacgc gctggcgctg      600
ccgctgcact ggcgcgttcc gcgcatcgaa gcgcgctggt ttatcgaagt ttatgaacag      660
gaagctaata tgaacccgac cctgctgaag ctggcgaagc tggatttcaa catggttcaa      720
agcattcatc aaaaggagat cggcgagctg gcccgctggt gggtgaccac gggtttggac      780
aagctggact ttgcacgtaa taatctgttg caaagctaca tgtggagctg cgctatcgca      840
tccgacccga aatttaagtt ggcacgtgaa accatcgttg aaattggtag cgtgctgact      900
gtggtggatg acggttacga tgtttacggt agcatggacg aactggacct gtacacgtcg      960
agcgtcgagc gctggagctg tgtcaaaatt gataagctgc cgaacacgct gaaactgatc     1020
ttcatgagca tgttcaacaa aaccaacgaa gtgggcctgc gcgtgcagca cgaacgtggc     1080
tataatagca ttccgacgtt tatcaaggca tgggtggagc aatgtaaaag ctaccaaaaa     1140
gaggcccgtt ggtttcatgg cggccatacc ccgcctctgg aggaatatag cctgaacggc     1200
ctggtgtcca ttggttttcc gctgctgctg atcaccggct acgtggcaat cgcggaaaat     1260
gaagccgcgc tggacaaggt ccatccactg ccggacctgt tgcattatag ctctctgctg     1320
agccgtctga tcaatgatat cggtacgagc ccggacgaga tggctcgtgg tgacaacctg     1380
aaaagcatcc attgttatat gaacgagacg ggtgcgtccg aagaggtcgc ccgcgagcat     1440
atcaagggcg ttattgagga gaactggaaa atcctgaatc aatgttgctt cgatcaaagc     1500
cagttccaag agccgttcat cacgttcaat ctgaacagcg ttcgcggtag ccactttttc     1560
tacgaatttg gcgacggttt tggcgttacg gacagctgga ccaaagttga tatgaaatcc     1620
gttctgatcg acccgatccc gttgggtgaa gagtag                                1656

<210> SEQ ID NO 5
<211> LENGTH: 1064
<212> TYPE: DNA
<213> ORGANISM: Santalum album

<400> SEQUENCE: 5
cccccgccat gagagctcca ttcattgatc atactgatca tgtgaatctc agaactgata       60
acgattcctc agagaatcga aggatgggga attataaacc cagtatttgg aactatgatt      120
ttttgcaatc gcttgcgact cgccacaata ttatggaaga gaggcatcta aagctagctg      180
agaagctgaa gggccaagtg aagtttatgt ttggggcacc aatggagccg ttagcaaagc      240
tggagcttgt ggatgtggtt caaaggctcg ggctaaacca ccgatttgag acagagatca      300
aggaagcgct atttagtatt tataaggatg agagcaatgg atggtggttt ggccacctcc      360
atgcgacatc tctccgattt aggctgctac gacagtgtgg gcttttatc ccccaggatg      420 tgtttaaaac atttcagagc aaaactggtg aatttgatat gaaactgtgt gacaatgtaa      480
aaggattgct gagcttgtat gaagcttcat tcttggggtg gagggatgaa acatcttag      540 atgaagccaa agccttcgcc accaagtact tgaaaaatgc atgggaaaac atatcccaaa     600
agtggcttgc caaagagtg aagcatgcac tggctttgcc tttgcactgg agagtcccta      660
gaatcgaagc tagatggttc gttgaggcat atggggaaga agagatatg aacccaacac      720 ttctcaaact tgcaaaattg gactttaaca tggtgcaatc aattcatcag aaagagattg      780
gggaattagc gaggtggtgg gtgactacgg ggttggataa gttagcgttt gctaggaata      840
atttactgca aagctatatg tggagctgcg cgattgcttc cgacccaaag ttcaaacttg      900
```

-continued

```
ctagagaaac tattgttgaa atcggaagtg tactcacagt tgttgacgat gcatatgacg      960
tctatggttc aatggatgaa cttgatctct acacgaactc cgttgaaagg tggagctgta     1020
cagaaattga caagttacca aacacattaa aattgatttt tatg                       1064
```

```
<210> SEQ ID NO 6
<211> LENGTH: 29
<212> TYPE: DNA
<213> ORGANISM: Artificial sequence
<220> FEATURE:
<223> OTHER INFORMATION: Primer synthesized on the basis of SCH5-Contig5.

<400> SEQUENCE: 6
cttcactctt ttggcaagcc acttttggg                                          29
```

```
<210> SEQ ID NO 7
<211> LENGTH: 30
<212> TYPE: DNA
<213> ORGANISM: Artificial sequence
<220> FEATURE:
<223> OTHER INFORMATION: Primer synthesized on the basis of SCH5-Contig5.

<400> SEQUENCE: 7
gtggcgaagg ctttggcttc atctaagatg                                         30
```

```
<210> SEQ ID NO 8
<211> LENGTH: 31
<212> TYPE: DNA
<213> ORGANISM: Artificial sequence
<220> FEATURE:
<223> OTHER INFORMATION: Primer synthesized on the basis of SCH5-Contig5

<400> SEQUENCE: 8
gcatatgacg tctatggttc aatggatgaa c                                       31
```

```
<210> SEQ ID NO 9
<211> LENGTH: 30
<212> TYPE: DNA
<213> ORGANISM: Artificial sequence
<220> FEATURE:
<223> OTHER INFORMATION: Primer synthesized on the basis of SCH5-Contig5

<400> SEQUENCE: 9
gttgaaaggt ggagctgtac agaaattgac                                         30
```

```
<210> SEQ ID NO 10
<211> LENGTH: 610
<212> TYPE: DNA
<213> ORGANISM: Santalum album

<400> SEQUENCE: 10
acaaaataaa tctcttgttc tgttctttgg atctcgtttt cttccctca gctctctcac        60 taatggattc ttccaccgcc accgccatga gagctccatt cattgatcat actgatcatg      120
tgaatctcag aactgataac gattcctcag agaatcgaag gatggggaat tataaaccca      180
gtatttggaa ctatgatttt ttgcaatcgc ttgcgactcg ccacaatatt atggaagaga      240
ggcatctaaa gctagctgag aagctgaagg gccaagtgaa gtttatgttt ggggcaccaa      300
tggagccgtt agcaaagctg agcttgtgg atgtggttca aaggctcggg ctaaaccacc       360
gatttgagac agagatcaag gaagcgctat ttagtattta taaggatgag agcaatggat      420
ggtggtttgg ccacctccat gcgacatctc tccgatttag gctgctacga cagtgtgggc      480
tttttatccc ccaggatgtg tttaaaacat ttcagagcaa aactggtgaa tttgatatga      540
```

```
aactgtgtga caatgtaaaa ggattgctga gcttgtatga agcttcattc ttggggtgga    600
gggatgaaaa                                                            610
```

<210> SEQ ID NO 11
<211> LENGTH: 1049
<212> TYPE: DNA
<213> ORGANISM: Santalum album

<400> SEQUENCE: 11

```
caagttacca aacacattaa aattgatttt tatgtctatg tttaacaaga ccaatgaagt     60
tggccttcga gtccagcatg agcgaggcta cagtggcatc actactttta tcaaagcgtg    120
ggttgaacag tgtaaatcgt accagaaaga agcaagatgg taccatgggg gacacacgcc    180
tccactggaa gaatatagct tgaatggact ggtttccata ggattccctc tcttgttgat    240
cacaggctac gtggcaatcg ctgagaacga ggctgcactg ataaagtgc accccttcc     300 tgatcttctg cactactcct ccctccttag tcgcctcatc aatgtatatg gaacctcttc    360
ggacgagttg gaaaggggag ataatctgaa gtcaattcaa tgttacatga accaaactgg    420
ggcttctgag aaagttgctc gtgagcacat aaagggaata atcgaggaaa actggaaaat    480
actgaatgag tgttgctttg atcaatctca gtttcaggag cctttttgaa cattcaattt    540
gaactctgtt cgagggtctc atttcttcta cgaatttgga gatggctttg ggtgacgga    600 tagctggaca aaggttgata tgaagtctgt tttgatcgat cctattcctc tcgacgagga    660
gtagaaaact caaagcttgt gcttggttta cggtaatagt gattcagtat aaatataaaa    720
atcggacgaa cttgaggaat atgtgaggca taactatttt taatgatcat gagttaaata    780
attaagaaat atctattcgg ctcatgattc ttgagtatat attattcctt atgcgttata    840
tttccatcaa ataattagtc cgctcctgta agtcgactgt aacattactc taagggtcgc    900
tattggtttt atgttatatt aagtctacta gtttgaagtg atggaataaa tgtttgtttt    960 taaggggggtt atgcactatg ttctcggttg ccttttacta ataaattttt tatgaaactc   1020
aaaaaaaaaa aaaaaaaaaa aaaaaaaaa                                     1049
```

<210> SEQ ID NO 12
<211> LENGTH: 2157
<212> TYPE: DNA
<213> ORGANISM: Santalum album

<400> SEQUENCE: 12

```
acaaaataaa tctcttgttc tgttctttgg atctcgtttt cttcccctca gctctctcac     60
taatggattc ttccaccgcc accgccatga gagctccatt cattgatcat actgatcatg    120
tgaatctcag aactgataac gattcctcag agaatcgaag gatggggaat tataaaccca    180
gtatttggaa ctatgatttt ttgcaatcgc ttgcgactcg ccacaatatt atggaagaga    240
ggcatctaaa gctagctgag aagctgaagg gccaagtgaa gttatgtttt ggggcaccaa    300
tggagccgtt agcaaagctg gagcttgtgg atgtggttca aaggctcggg ctaaaccacc    360
gatttgagac agagatcaag gaagcgctat ttagtatttta aaggatgag agcaatggat    420 ggtggtttgg ccacctccat gcgacatctc tccgatttag gctgctacga cagtgtgggc    480 ttttttatccc ccaggatgtg tttaaaacat ttcagagcaa aactggtgaa tttgatatga    540
aactgtgtga caatgtaaaa ggattgctga gcttgtatga agcttcattc ttggggtgga    600
gggatgaaaa catcttagat gaagccaaag ccttcgccac caagtacttg aaaaatgcat    660
```

| | |
|---|---|
| gggaaaacat atcccaaaag tggcttgcca aaagagtgaa gcatgcactg gctttgcctt | 720 |
| tgcactggag agtccctaga atcgaagcta gatggttcgt tgaggcatat ggggaagaag | 780 |
| agaatatgaa cccaacactt ctcaaacttg caaaattgga ctttaacatg gtgcaatcaa | 840 |
| ttcatcagaa agagattggg gaattagcga ggtggtgggt gactacgggg ttggataagt | 900 |
| tagcgtttgc taggaataat ttactgcaaa gctatatgtg gagctgcgcg attgcttccg | 960 |
| acccaaagtt caaacttgct agagaaacta ttgttgaaat cggaagtgta ctcacagttg | 1020 |
| ttgacgatgc atatgacgtc tatggttcaa tggatgaact tgatctctac acgaactccg | 1080 |
| ttgaaaggtg gagctgtaca gaaattgaca agttaccaaa cacattaaaa ttgattttta | 1140 |
| tgtctatgtt taacaagacc aatgaagttg gccttcgagt ccagcatgag cgaggctaca | 1200 |
| gtggcatcac tacttttatc aaagcgtggg ttgaacagtg taaatcgtac cagaaagaag | 1260 |
| caagatggta ccatggggga cacacgcctc cactggaaga atatagcttg aatggactgg | 1320 |
| tttccatagg attccctctc ttgttgatca caggctacgt ggcaatcgct gagaacgagg | 1380 |
| ctgcactgga taaagtgcac cccctttcctg atcttctgca ctactcctcc ctccttagtc | 1440 |
| gcctcatcaa tgatatggga acctcttcgg acgagttgga aaggggagat aatctgaagt | 1500 |
| caattcaatg ttacatgaac caaactgggg cttctgagaa agttgctcgt gagcacataa | 1560 |
| agggaataat cgaggaaaac tggaaaatac tgaatgagtg ttgctttgat caatctcagt | 1620 |
| ttcaggagcc ttttgtaaca ttcaatttga actctgttcg agggtctcat ttcttctacg | 1680 |
| aatttggaga tggctttggg gtgacggata gctggacaaa ggttgatatg aagtctgttt | 1740 |
| tgatcgatcc tattcctctc gacgaggagt agaaaaactca aagcttgtgc ttggtttacg | 1800 |
| gtaatagtga ttcagtataa atataaaaat cggacgaact tgaggaatat gtgaggcata | 1860 |
| actattttta atgatcatga gttaaataat taagaaatat ctattcggct catgattctt | 1920 |
| gagtatatat tattccttat gcgttatatt tccatcaaat aattagtccg ctcctgtaag | 1980 |
| tcgactgtaa cattactcta agggtcgcta ttggttttat gttatattaa gtctactagt | 2040 |
| ttgaagtgat ggaataaatg tttgttttta aggggggttat gcactatgtt ctcggttgcc | 2100 |
| ttttactaat aaattttta tgaaactcaa aaaaaaaaaa aaaaaaaaaa aaaaaaa | 2157 |

<210> SEQ ID NO 13
<211> LENGTH: 569
<212> TYPE: PRT
<213> ORGANISM: Santalum album

<400> SEQUENCE: 13

Met Asp Ser Ser Thr Ala Thr Ala Met Arg Ala Pro Phe Ile Asp His
1               5                   10                  15

Thr Asp His Val Asn Leu Arg Thr Asp Asn Asp Ser Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr Arg His Asn Ile Met Glu Glu Arg His Leu Lys Leu
    50                  55                  60

Ala Glu Lys Leu Lys Gly Gln Val Lys Phe Met Phe Gly Ala Pro Met
65                  70                  75                  80

Glu Pro Leu Ala Lys Leu Glu Leu Val Asp Val Gln Arg Leu Gly
                85                  90                  95

Leu Asn His Arg Phe Glu Thr Glu Ile Lys Glu Ala Leu Phe Ser Ile
            100                 105                 110

-continued

```
Tyr Lys Asp Glu Ser Asn Gly Trp Phe Gly His Leu His Ala Thr
    115                 120                 125
Ser Leu Arg Phe Arg Leu Leu Arg Gln Cys Gly Leu Phe Ile Pro Gln
    130                 135                 140
Asp Val Phe Lys Thr Phe Gln Ser Lys Thr Gly Glu Phe Asp Met Lys
145                 150                 155                 160
Leu Cys Asp Asn Val Lys Gly Leu Leu Ser Leu Tyr Glu Ala Ser Phe
                165                 170                 175
Leu Gly Trp Arg Asp Glu Asn Ile Leu Asp Glu Ala Lys Ala Phe Ala
            180                 185                 190
Thr Lys Tyr Leu Lys Asn Ala Trp Glu Asn Ile Ser Gln Lys Trp Leu
        195                 200                 205
Ala Lys Arg Val Lys His Ala Leu Ala Leu Pro Leu His Trp Arg Val
    210                 215                 220
Pro Arg Ile Glu Ala Arg Trp Phe Val Glu Ala Tyr Gly Glu Glu Glu
225                 230                 235                 240
Asn Met Asn Pro Thr Leu Leu Lys Leu Ala Lys Leu Asp Phe Asn Met
                245                 250                 255
Val Gln Ser Ile His Gln Lys Glu Ile Gly Glu Leu Ala Arg Trp Trp
            260                 265                 270
Val Thr Thr Gly Leu Asp Lys Leu Ala Phe Ala Arg Asn Asn Leu Leu
        275                 280                 285
Gln Ser Tyr Met Trp Ser Cys Ala Ile Ala Ser Asp Pro Lys Phe Lys
    290                 295                 300
Leu Ala Arg Glu Thr Ile Val Glu Ile Gly Ser Val Leu Thr Val Val
305                 310                 315                 320
Asp Asp Ala Tyr Asp Val Tyr Gly Ser Met Asp Glu Leu Asp Leu Tyr
                325                 330                 335
Thr Asn Ser Val Glu Arg Trp Ser Cys Thr Glu Ile Asp Lys Leu Pro
            340                 345                 350
Asn Thr Leu Lys Leu Ile Phe Met Ser Met Phe Asn Lys Thr Asn Glu
        355                 360                 365
Val Gly Leu Arg Val Gln His Glu Arg Gly Tyr Ser Gly Ile Thr Thr
    370                 375                 380
Phe Ile Lys Ala Trp Val Glu Gln Cys Lys Ser Tyr Gln Lys Glu Ala
385                 390                 395                 400
Arg Trp Tyr His Gly His Thr Pro Pro Leu Glu Glu Tyr Ser Leu
                405                 410                 415
Asn Gly Leu Val Ser Ile Gly Phe Pro Leu Leu Leu Ile Thr Gly Tyr
            420                 425                 430
Val Ala Ile Ala Glu Asn Glu Ala Ala Leu Asp Lys Val His Pro Leu
        435                 440                 445
Pro Asp Leu Leu His Tyr Ser Ser Leu Leu Ser Arg Leu Ile Asn Asp
    450                 455                 460
Met Gly Thr Ser Ser Asp Glu Leu Glu Arg Gly Asp Asn Leu Lys Ser
465                 470                 475                 480
Ile Gln Cys Tyr Met Asn Gln Thr Gly Ala Ser Glu Lys Val Ala Arg
                485                 490                 495
Glu His Ile Lys Gly Ile Ile Glu Glu Asn Trp Lys Ile Leu Asn Glu
            500                 505                 510
Cys Cys Phe Asp Gln Ser Gln Phe Gln Glu Pro Phe Val Thr Phe Asn
        515                 520                 525
Leu Asn Ser Val Arg Gly Ser His Phe Phe Tyr Glu Phe Gly Asp Gly
```

Phe Gly Val Thr Asp Ser Trp Thr Lys Val Asp Met Lys Ser Val Leu
545                 550                 555                 560

Ile Asp Pro Ile Pro Leu Asp Glu Glu
                565

<210> SEQ ID NO 14
<211> LENGTH: 1710
<212> TYPE: DNA
<213> ORGANISM: Santalum album

<400> SEQUENCE: 14

```
atggattctt ccaccgccac cgccatgaga gctccattca ttgatcatac tgatcatgtg     60
aatctcagaa ctgataacga ttcctcagag aatcgaagga tggggaatta taaacccagt    120
atttggaact atgatttttt gcaatcgctt gcgactcgcc acaatattat ggaagagagg    180
catctaaagc tagctgagaa gctgaagggc caagtgaagt ttatgttttgg ggcaccaatg    240
gagccgttag caaagctgga gcttgtggat gtggttcaaa ggctcgggct aaaccaccga    300
tttgagacag agatcaagga agcgctattt agtatttata aggatgagag caatggatgg    360
tggtttggcc acctccatgc gacatctctc cgatttaggc tgctacgaca gtgtgggctt    420
tttatccccc aggatgtgtt taaaacattt cagagcaaaa ctggtgaatt tgatatgaaa    480
ctgtgtgaca atgtaaaagg attgctgagc ttgtatgaag cttcattctt ggggtggagg    540
gatgaaaaca tcttagatga agccaaagcc ttcgccacca gtacttgaaa aaatgcatgg    600
gaaaacatat cccaaaagtg gcttgccaaa gagtgaagc atgcactggc tttgcctttg    660
cactggagag tccctagaat cgaagctaga tggttcgttg aggcatatgg ggaagaagag    720
aatatgaacc aacacttcct caaacttgca aaattggact taacatggt gcaatcaatt    780
catcagaaag agattgggga attagcgagg tggtgggtga ctacgggggt ggataagtta    840
gcgtttgcta ggaataattt actgcaaagc tatatgtgga gctgcgcgat tgcttccgac    900
ccaaagttca aacttgctag agaaactatt gttgaaatcg aagtgtact cacagttgtt    960
gacgatgcat atgacgtcta tggttcaatg gatgaacttg atctctacac gaactccgtt   1020
gaaaggtgga gctgtacaga aattgacaag ttaccaaaca cattaaaatt gattttatg   1080
gctatgttta caagaccaa tgaagttggc cttcgagtcc agcatgagcg aggctacagc   1140
ggcatcacta ctttttatcaa gcatggggtt gaacagtgta atcgtacca gaaagaagca   1200
agatggtacc atgggggaca cacgcctcca ctggaagaat atagcttgaa tggacttgtt   1260
tccataggat cccctctctt gttgatcaca ggctacgtgg caatcgctga aacgaggct   1320
gcactggata aagtgcaccc ccttcctgat cttctgcact actcctcctt ccttagtcgc   1380
ctcatcaatg atatgggaac tcttcggac gagttggaaa ggggagataa tctgaagtca   1440
attcaatgtt acatgaacca aactggggct tctgagaaag ttgctcgtga gcacataaag   1500
ggaataatcg aggaaaactg gaaaatactg aatgagtgtt gctttgatca atctcagttt   1560
caggagcctt tgtaacatt caatttgaac tctgttcgag gtctcatttt cttctacgaa   1620
tttggagatg gctttgggt gacgaatagc tggacaaagg ttgatatgaa gtctgttttg   1680
atcgatccta ttcctctcga cgaggagtag                                    1710
```

<210> SEQ ID NO 15
<211> LENGTH: 569
<212> TYPE: PRT
<213> ORGANISM: Santalum album

<400> SEQUENCE: 15

Met Asp Ser Ser Thr Ala Thr Ala Met Arg Ala Pro Phe Ile Asp His
1               5                   10                  15

Thr Asp His Val Asn Leu Arg Thr Asp Asn Asp Ser Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr Arg His Asn Ile Met Glu Glu Arg His Leu Lys Leu
    50                  55                  60

Ala Glu Lys Leu Lys Gly Gln Val Lys Phe Met Phe Gly Ala Pro Met
65                  70                  75                  80

Glu Pro Leu Ala Lys Leu Glu Leu Val Asp Val Val Gln Arg Leu Gly
                85                  90                  95

Leu Asn His Arg Phe Glu Thr Glu Ile Lys Glu Ala Leu Phe Ser Ile
            100                 105                 110

Tyr Lys Asp Glu Ser Asn Gly Trp Trp Phe Gly His Leu His Ala Thr
        115                 120                 125

Ser Leu Arg Phe Arg Leu Leu Arg Gln Cys Gly Leu Phe Ile Pro Gln
    130                 135                 140

Asp Val Phe Lys Thr Phe Gln Ser Lys Thr Gly Glu Phe Asp Met Lys
145                 150                 155                 160

Leu Cys Asp Asn Val Lys Gly Leu Leu Ser Leu Tyr Glu Ala Ser Phe
                165                 170                 175

Leu Gly Trp Arg Asp Glu Asn Ile Leu Asp Glu Ala Lys Ala Phe Ala
            180                 185                 190

Thr Lys Tyr Leu Lys Asn Ala Trp Glu Asn Ile Ser Gln Lys Trp Leu
        195                 200                 205

Ala Lys Arg Val Lys His Ala Leu Ala Leu Pro Leu His Trp Arg Val
    210                 215                 220

Pro Arg Ile Glu Ala Arg Trp Phe Val Glu Ala Tyr Gly Glu Glu Glu
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Ala Phe Ala Arg Asn Asn Leu Leu
        275                 280                 285

Gln Ser Tyr Met Trp Ser Cys Ala Ile Ala Ser Asp Pro Lys Phe Lys
    290                 295                 300

Leu Ala Arg Glu Thr Ile Val Glu Ile Gly Ser Val Leu Thr Val Val
305                 310                 315                 320

Asp Asp Ala Tyr Asp Val Tyr Gly Ser Met Asp Glu Leu Asp Leu Tyr
                325                 330                 335

Thr Asn Ser Val Glu Arg Trp Ser Cys Thr Ile Asp Lys Leu Pro
            340                 345                 350

Asn Thr Leu Lys Leu Ile Phe Met Ala Met Phe Asn Lys Thr Asn Glu
        355                 360                 365

Val Gly Leu Arg Val Gln His Glu Arg Gly Tyr Ser Gly Ile Thr Thr
    370                 375                 380

Phe Ile Lys Ala Trp Val Glu Gln Cys Lys Ser Tyr Gln Lys Glu Ala
385                 390                 395                 400

Arg Trp Tyr His Gly Gly His Thr Pro Pro Leu Glu Glu Tyr Ser Leu

```
                    405                 410                 415
Asn Gly Leu Val Ser Ile Gly Phe Pro Leu Leu Ile Thr Gly Tyr
            420                 425                 430

Val Ala Ile Ala Glu Asn Glu Ala Ala Leu Asp Lys Val His Pro Leu
            435                 440                 445

Pro Asp Leu Leu His Tyr Ser Ser Leu Ser Arg Leu Ile Asn Asp
450                 455                 460

Met Gly Thr Ser Ser Asp Glu Leu Glu Arg Gly Asp Asn Leu Lys Ser
465                 470                 475                 480

Ile Gln Cys Tyr Met Asn Gln Thr Gly Ala Ser Glu Lys Val Ala Arg
                485                 490                 495

Glu His Ile Lys Gly Ile Ile Glu Glu Asn Trp Lys Ile Leu Asn Glu
            500                 505                 510

Cys Cys Phe Asp Gln Ser Gln Phe Gln Glu Pro Phe Val Thr Phe Asn
            515                 520                 525

Leu Asn Ser Val Arg Gly Ser His Phe Phe Tyr Glu Phe Gly Asp Gly
            530                 535                 540

Phe Gly Val Thr Asn Ser Trp Thr Lys Val Asp Met Lys Ser Val Leu
545                 550                 555                 560

Ile Asp Pro Ile Pro Leu Asp Glu Glu
                565

<210> SEQ ID NO 16
<211> LENGTH: 34
<212> TYPE: DNA
<213> ORGANISM: Artificial sequence
<220> FEATURE:
<223> OTHER INFORMATION: Primer

<400> SEQUENCE: 16
ctagccatgg cttcagaaaa agaaattagg agag                              34

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
ccggaattcc tatttgcttc tcttgtaaac tttgttcaag                        40

<210> SEQ ID NO 18
<211> LENGTH: 42
<212> TYPE: DNA
<213> ORGANISM: Artificial sequence
<220> FEATURE:
<223> OTHER INFORMATION: Primer

<400> SEQUENCE: 18
aaggagatat acatatgaca aaaaaagttg gtgtcggtca gg                     42

<210> SEQ ID NO 19
<211> LENGTH: 43
<212> TYPE: DNA
<213> ORGANISM: Artificial sequence
<220> FEATURE:
<223> OTHER INFORMATION: Primer

<400> SEQUENCE: 19
ctttaccaga ctcgagttac gccttttttca tctgatcctt tgc                   43
```

<210> SEQ ID NO 20
<211> LENGTH: 35
<212> TYPE: DNA
<213> ORGANISM: Artificial sequence
<220> FEATURE:
<223> OTHER INFORMATION: Primer

<400> SEQUENCE: 20 cccggggat ccatggctac cgataatgac agctc                          35

<210> SEQ ID NO 21
<211> LENGTH: 23
<212> TYPE: DNA
<213> ORGANISM: Artificial sequence
<220> FEATURE:
<223> OTHER INFORMATION: Primer

<400> SEQUENCE: 21
caccgctgag caataactag cat                                      23

<210> SEQ ID NO 22
<211> LENGTH: 383
<212> TYPE: DNA
<213> ORGANISM: Santalum album

<400> SEQUENCE: 22
gatcaaggaa gcgctgttta gtatttacaa ggatgggagc aatggatggt ggtttggcca    60
ccttcatgcg acatctctcc gatttaggct gctacgacag tgtgggcttt ttattcccca   120
agatgtgttt aaaacgttcc aaaacaaaac tggggaattt gatatgaaac tgtgggacaa   180
cgtaaaaggg ctgctgagct tatatgaagc ttcatacttg ggatggaagg gtgaaaacat   240
cctagatgaa gccaaggcct tcaccaccaa gtgcttgaaa agtgcatggg aaaatatatc   300
cgaaaagtgg ttagccaaaa gagtgaagca tgcattggct ttgcctttgc attggagagt   360
ccctcgaatc gaagctagat ggt                                          383

<210> SEQ ID NO 23
<211> LENGTH: 26
<212> TYPE: DNA
<213> ORGANISM: Artificial sequence
<220> FEATURE:
<223> OTHER INFORMATION: Primer

<400> SEQUENCE: 23
ccgaaaagtg gttagccaaa agagtg                                    26

<210> SEQ ID NO 24
<211> LENGTH: 23
<212> TYPE: DNA
<213> ORGANISM: Artificial sequence
<220> FEATURE:
<223> OTHER INFORMATION: Primer

<400> SEQUENCE: 24
cgggtcggaa gcaatcgcgc agc                                       23

<210> SEQ ID NO 25
<211> LENGTH: 26
<212> TYPE: DNA
<213> ORGANISM: Artificial sequence
<220> FEATURE:
<223> OTHER INFORMATION: Primer

```
<400> SEQUENCE: 25
ccgatttcga caatagtttc tctagc                                          26

<210> SEQ ID NO 26
<211> LENGTH: 1725
<212> TYPE: DNA
<213> ORGANISM: Santalum album

<400> SEQUENCE: 26
actaatggat tcttccaccg ccaccgccat gacagctcca ttcattgatc ctactgatca     60
tgtgaatctc aaaactgata ctgatgcctc agagaatcga aggatgggaa attataaacc    120
cagcatttgg aattatgatt ttttacaatc acttgcaact catcacaata ttgtggaaga    180
gaggcatcta aagctagctg agaagctgaa gggccaagtg aagtttatgt ttggggcacc    240
aatggagccg ttagcaaagc tggagcttgt ggatgtggtt caaaggcttg gctaaaccca    300
cctatttgag acagagatca aggaagcgct gtttagtatt tacaaggatg ggagcaatgg    360
atggtggttt ggccaccttc atgcgacatc tctccgattt aggctgctac gacagtgtgg    420 gcttttatt cccaagatg tgtttaaaac gttccaaaac aaaactgggg aatttgatat      480
gaaactgtgg gacaacgtaa aagggctgct gagcttatat gaagcttcat acttgggatg    540
gaagggtgaa acatcctag atgaagccaa ggccttcacc accaagtgct tgaaaagtgc     600
atgggaaaat atatccgaaa agtggttagc caaaagagtg aagcatgcat ggctttgcc    660 tttgcattgg agagtccctc gaatcgaagc tagatggttc attgaggtat atgagcaaga    720
agcgaatatg aacccaacac tactcaaact cgcaaaatta gactttaata tggtgcaatc    780
aattcatcag aaagagattg gggaattagc aaggtggtgg gtgactactg cttggataa     840 gttagacttt gctaggaata atttactgca gagctatatg tggagctgcc cgattgcttc    900
cgacccgaag ttcaaacttg ctagagaaac tattgtcgaa atcggaagtg tactcacagt    960
tgttgacgat ggatatgacg tctatggttc aatggacgaa cttgatctct acacaagctc   1020
cgttgaaagg tggagctgtg tgaaaattga caagttgcca aacacgttaa aattaatttt   1080
tatgtctatg ttcaacaaga ccaatgaggt tggtcttcga gtccagcatg agcgaggcta   1140
caatagcatc cctacttta tcaaagcgtg ggttgaacag tgtaaatcat accagaaaga    1200
agcaagatgg ttccacgggg gacacacgcc tccattggaa gaatatagct tgaatggact   1260
tgtttccata ggattccctc tcttgttaat cacaggctac gtggcaatcg ctgagaacga   1320
ggctgcactg gataaagtgc acccccttcc tgatcttctg cactactcct cctccttag    1380 tcgcctcatc aatgatatag gaacgtctcc ggatgagatg gcaagaggcg ataatctgaa   1440
gtcaatccat tgttacatga acgaaactgg ggcttcgag gaagttgctc gtgagcacat    1500
aaagggagta atcgaggaga attggaaaat actgaatcag tgctgctttg atcaatctca   1560
gtttcaggag ccttttataa ccttcaattt gaactctgtt cgagggtctc atttcttcta   1620
tgaatttggg gatggctttg gggtgacgga tagctggaca aaggttgata tgaagtccgt   1680
tttgatcgac cctattcctc tcggcgagga gtagtaagct cgaag                   1725

<210> SEQ ID NO 27
<211> LENGTH: 569
<212> TYPE: PRT
<213> ORGANISM: Santalum album

<400> SEQUENCE: 27

Met Asp Ser Ser Thr Ala Thr Ala Met Thr Ala Pro Phe Ile Asp Pro
```

```
1               5                   10                  15
Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
            35                  40                  45

Ser Leu Ala Thr His His Asn Ile Val Glu Glu Arg His Leu Lys Leu
            50                  55                  60

Ala Glu Lys Leu Lys Gly Gln Val Lys Phe Met Phe Gly Ala Pro Met
65                      70                  75                  80

Glu Pro Leu Ala Lys Leu Glu Leu Val Asp Val Val Gln Arg Leu Gly
                    85                  90                  95

Leu Asn His Leu Phe Glu Thr Glu Ile Lys Glu Ala Leu Phe Ser Ile
                100                 105                 110

Tyr Lys Asp Gly Ser Asn Gly Trp Trp Phe Gly His Leu His Ala Thr
                115                 120                 125

Ser Leu Arg Phe Arg Leu Leu Arg Gln Cys Gly Leu Phe Ile Pro Gln
            130                 135                 140

Asp Val Phe Lys Thr Phe Gln Asn Lys Thr Gly Glu Phe Asp Met Lys
145                 150                 155                 160

Leu Trp Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Thr
            180                 185                 190

Thr Lys Cys Leu Lys Ser Ala Trp Glu Asn Ile Ser Glu Lys Trp Leu
        195                 200                 205

Ala Lys Arg Val Lys His Ala Leu Ala Leu Pro Leu His Trp Arg Val
210                 215                 220

Pro Arg Ile Glu Ala Arg Trp Phe Ile Glu Val Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
                260                 265                 270

Val Thr Thr Gly Leu Asp Lys Leu Asp Phe Ala Arg Asn Asn Leu Leu
        275                 280                 285

Gln Ser Tyr Met Trp Ser Cys Pro Ile Ala Ser Asp Pro Lys Phe Lys
            290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Met Asp Glu Leu Asp Leu Tyr
                325                 330                 335

Thr Ser Ser Val Glu Arg Trp Ser Cys Val Lys Ile Asp Lys Leu Pro
            340                 345                 350

Asn Thr Leu Lys Leu Ile Phe Met Ser Met Phe Asn Lys Thr Asn Glu
            355                 360                 365

Val Gly Leu Arg Val Gln His Glu Arg Gly Tyr Asn Ser Ile Pro Thr
            370                 375                 380

Phe Ile Lys Ala Trp Val Glu Gln Cys Lys Ser Tyr Gln Lys Glu Ala
385                 390                 395                 400

Arg Trp Phe His Gly Gly His Thr Pro Leu Glu Glu Tyr Ser Leu
                405                 410                 415

Asn Gly Leu Val Ser Ile Gly Phe Pro Leu Leu Leu Ile Thr Gly Tyr
            420                 425                 430
```

-continued

```
Val Ala Ile Ala Glu Asn Glu Ala Ala Leu Asp Lys Val His Pro Leu
        435                 440                 445
Pro Asp Leu Leu His Tyr Ser Ser Leu Leu Ser Arg Leu Ile Asn Asp
    450                 455                 460
Ile Gly Thr Ser Pro Asp Glu Met Ala Arg Gly Asp Asn Leu Lys Ser
465                 470                 475                 480
Ile His Cys Tyr Met Asn Glu Thr Gly Ala Ser Glu Glu Val Ala Arg
                485                 490                 495
Glu His Ile Lys Gly Val Ile Glu Glu Asn Trp Lys Ile Leu Asn Gln
            500                 505                 510
Cys Cys Phe Asp Gln Ser Gln Phe Gln Glu Pro Phe Ile Thr Phe Asn
        515                 520                 525
Leu Asn Ser Val Arg Gly Ser His Phe Phe Tyr Glu Phe Gly Asp Gly
    530                 535                 540
Phe Gly Val Thr Asp Ser Trp Thr Lys Val Asp Met Lys Ser Val Leu
545                 550                 555                 560
Ile Asp Pro Ile Pro Leu Gly Glu Glu
                565
```

METHOD FOR PRODUCING BETA-SANTALENE

CROSS-REFERENCE TO RELATED APPLICATIONS

This application is a divisional of U.S. patent application Ser. No. 14/530,651 filed Oct. 31, 2014, now U.S. Pat. No. 9,777,293 issued Oct. 3, 2017, which is a continuation of U.S. patent application Ser. No. 13/124,866 filed Apr. 19, 2011, now U.S. Pat. No. 8,877,461 issued Nov. 4, 2014, which is a national stage application under 35 U.S.C. § 371 of International Patent Application PCT/IB/2009/055589 filed on Dec. 9, 2009, which claims priority from EP08171298.6, filed on Dec. 11, 2008 and from PCT/IB/2009/053623 filed on Aug. 17, 2009. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 7530US_DIV_Sequence Listing. The size of the text file is 43 KB, and the text file was created on Aug. 21, 2017.

TECHNICAL FIELD

The present invention provides a method of producing β-santalene, said method comprising contacting at least one polypeptide with farnesyl pyrophosphate (FPP). In particular, said method may be carried out in vitro or in vivo to produce β-santalene, a very useful compound in the fields of perfumery and flavoring. The present invention also provides the amino acid sequence of a polypeptide useful in the method of the invention. A nucleic acid encoding the polypeptide of the invention and an expression vector containing said nucleic acid are also part of the present invention. A non-human host organism or a cell transformed to be used in the method of producing β-santalene is also an object of the present invention.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Over 300 sesquiterpene hydrocarbons and 3000 sesquiterpenoids have been identified (Joulain, D., and König, W. A., *The Atlas of Spectral Data of Sesquiterpene Hydrocarbons*, EB Verlag, Hamburg, 1998; Connolly, J. D., Hill R. A., *Dictionary of Terpenoids*, Vol 1, Chapman and Hall (publisher), 1991), and many new structures are identified each year. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. There is virtually an infinity of sesquiterpene synthases present in the plant kingdom, all using the same substrate (farnesyl pyrophosphate, FPP) but having different product profiles. Genes and cDNAs encoding sesquiterpene synthases have been cloned and the corresponding recombinant enzymes characterized. The biosynthesis of terpenes in plants and other organisms has been extensively studied and is not further detailed in here, but reference is made to Dewick, *Nat. Prod. Rep.,* 2002, 19, 181-222, which reviews the state of the art of terpene biosynthetic pathways.

β-Santalene is a naturally occurring sesquiterpene molecule that can be used as starting material for the chemical synthesis or the biosynthesis of β-santalol (as represented in FIG. 2B), which is a major constituent of sandalwood oil. Sandalwood oil is an important perfumery ingredient obtained by distillation of the heartwood of *Santalum* species. Sandalwood is also largely used for incenses and traditional medicine. The oil contains 90% of sesquiterpene alcohols. Among the different isomers of santalol, β-santalol is the principal contributor to the typical sweet-woody and balsamic odour of sandalwood oil. Other constituents such as epi-β-santalol and α-santalol may also contribute to the sandalwood note.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years. Due to over-exploitation of the natural resources, difficulties of cultivation, slow growth of the *Santalum* plants, the availabilities of sandalwood raw material has dramatically decreased during the past decades. Therefore, it would be an advantage to provide a source of β-santalol, which is less subjected to fluctuations in availability and quality. A chemical synthesis of the sandalwood sesquiterpene constituents is so far not available. A biochemical pathway leading to the synthesis of β-santalene, which could then be used to produce β-santalol, would therefore be of great interest.

Santalane type sesquiterpene, and particularly sesquiterpenes with the β-santalane skeleton, were identified in several plant species. Though, no sesquiterpene synthase capable of producing β-santalene, has yet been described.

A sesquiterpene synthase capable of synthesizing at least one bi-cyclic and/or tri-cyclic sesquiterpene having a santalane carbon skeleton, the corresponding nucleic acid and a method for producing such compound having a santalane carbon skeleton are disclosed in the International patent application WO 2006/134523. Nevertheless, no trace of β-santalene was detected as product of the sesquiterpene synthases disclosed in the examples. The only product with a santalane skeleton was epi-beta-santalene. The properties of epi-beta-santalene are very different from those of β-santalene. In particular, it is of no interest in the synthesis of β-santalol. Moreover, the sesquiterpene synthase disclosed in WO 2006/134523 shares only 27% of identity with the sequence of the invention.

The percentage of identity between sesquiterpene synthases known from the databases and the polypeptides of the invention is very low. The closest protein sequence to the β-santalene synthase of the invention is a monoterpene synthase from *Santalum album* (access No. ACF24767; Jones, C. G., Keeling, C. I., Ghisalberti, E. L., Barbour, E.

L., Plummer, J. A. and Bohlmann, J. Arch. Biochem. Biophys., 2008, 477(1), 121-130) which shares 58% amino acid sequence identity with the β-santalene synthase of the invention. When contacted with FPP, this enzyme produces over 90% of β-bisabolene and no santalene isomer is formed.

In addition to the difference between the sequences themselves, it also has to be pointed out that the structure and the properties of the products synthesized by the above-mentioned enzyme are very different from those of the sesquiterpene β-santalene. In particular the monoterpenes produced by this enzyme, i.e. alpha-terpineol, limonene, geraniol, myrcene, linalool and some other minor products are not suitable as a starting material for the synthesis of β-santalol, which is a very useful ingredient in the field of perfumery.

Despite extensive studies of terpene cyclization, the isolation and characterization of the terpene synthases is still difficult, particularly in plants, due to their low abundance, their often transient expression patterns, and the complexity of purifying them from the mixtures of resins and phenolic compounds in tissues where they are expressed.

It is an objective of the present invention to provide methods for making β-santalene in an economic way, as indicated above. Accordingly, the present invention has the objective to produce β-santalene while having little waste, a more energy and resource efficient process and while reducing dependency on fossil fuels. It is a further objective to provide enzymes capable of synthesizing β-santalene, which is useful as perfumery and/or aroma ingredients.

ABBREVIATIONS USED

ACC 1-aminocyclopropanecarboxylic acid
bp base pair
kb kilo base
BSA bovine serum albumin
2,4D 2,4-dichlorophenoxyacetic acid
DNA deoxyribonucleic acid
cDNA complementary DNA
dNTP deoxy nucleotide triphosphate
DTT dithiothreitol
EDTA ethylene-diamine-tetraacetic acid
FPP farnesyl pyrophosphate
GC gaseous chromatograph
IPTG isopropyl-D-thiogalacto-pyranoside
Kin kinetin
LB lysogeny broth
MS mass spectrometer
PCR polymerase chain reaction
RMCE recombinase-mediated cassette exchange
3'-/5'-RACE 3' and 5' rapid amplification of cDNA ends
RNA ribonucleic acid
mRNA messenger ribonucleic acid
RNAse Ribonuclease

DESCRIPTION OF THE INVENTION

The present invention provides a method to biosynthetically produce β-santalene in an economic, reliable and reproducible way, using a polypeptide having a β-santalene synthase activity. The present invention is particularly useful because no such polypeptide was known in the prior art and because no such biosynthesis of β-santalene has been described. This solves the very important problem of the supply of β-santalene, a compound which is very useful for the perfumery industry. The present invention also provides a nucleic acid sequence that encodes the polypeptides used in the method of the invention, thus being intimately linked to said polypeptide. The polypeptide and the nucleic acid are very important tools, which are both necessary to carry out the method of the invention. The same is true for vectors and for organisms modified with the nucleic acid of the invention to heterologously express the polypeptide of the invention.

A "sesquiterpene synthase" or a "polypeptide having a sesquiterpene synthase activity" is intended for the purpose of the present application as a polypeptide capable of catalyzing the synthesis of a sesquiterpene molecule or of a mixture of sesquiterpene molecules from the acyclic terpene precursor FPP.

As a "β-santalene synthase" or as a "polypeptide having a β-santalene synthase activity", we mean here a polypeptide capable of catalyzing the synthesis of β-santalene, in the form of any of its stereoisomers or a mixture thereof, starting from FPP. B-Santalene may be the only product or may be part of a mixture of sesquiterpenes. B-Santalene is defined by the way of its structure, as represented in FIG. 2A.

The ability of a polypeptide to catalyze the synthesis of a particular sesquiterpene (for example β-santalene) can be simply confirmed by performing the enzyme assay as detailed in Example 3.

According to the present invention, polypeptides are also meant to include truncated polypeptides provided that they keep their sesquiterpene synthase activity as defined in any of the above embodiments and that they share at least the defined percentage of identity with the corresponding fragment of SEQ ID NO:15.

As intended herein below, "a nucleotide sequence obtained by modifying SEQ ID NO:14 or 2" encompasses any sequence that has been obtained by changing the sequence of SEQ ID NO:14 or of SEQ ID NO:2 using any method known in the art, for example by introducing any type of mutations such as deletion, insertion or substitution mutations. Examples of such methods are cited in the part of the description relative to the variant polypeptides and the methods to prepare them.

According to the present invention, polypeptides are also meant to include truncated polypeptides provided that they keep their sesquiterpene synthase activity as defined in any of the above embodiments and that they share at least the defined percentage of identity with the corresponding fragment of SEQ ID NO:1.

As intended herein below, "a nucleotide sequence obtained by modifying SEQ ID NO:2, 4 or the complement thereof" encompasses any sequence that has been obtained by changing the sequence of SEQ ID NO:2, of SEQ ID NO:4 or of the complement thereof using any method known in the art, for example by introducing any type of mutations such as deletion, insertion or substitution mutations. Examples of such methods are cited in the part of the description relative to the variant polypeptides and the methods to prepare them.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the world wide web. Preferably, the BLAST program (Tatiana et al, *FEMS Microbiol Lett.*, 1999, 174:247-250, 1999) set to the default parameters, available from the National Center for Biotechnology Information (NCBI) at http://www.ncbi.nlm.nih.gov/BLAST/b12seq/wblast2.cgi, can be used to obtain an optimal alignment of peptidic or nucleotidic sequences and to calculate the percentage of sequence identity.

One object of the present invention is therefore a method for producing β-santalene comprising
a) contacting FPP with at least one polypeptide having a β-santalene synthase activity and comprising an amino acid sequence at least 50% identical to SEQ ID NO:1 or 3;
b) optionally, isolating the β-santalene produced in step a).

One object of the present invention is therefore a method for producing β-santalene comprising
a) contacting FPP with at least one polypeptide having a β-santalene synthase activity and comprising an amino acid sequence at least 60% identical to SEQ ID NO:15;
b) optionally, isolating the β-santalene produced in step a)

According to a preferred embodiment, β-santalene represents at least 20%, preferably at least 30%, preferably at least 35% of the products produced by the method of the invention.

The method can be carried out in vitro as well as in vivo, provided that methods involving only the natural metabolism of the plant, without any transformation, are not encompassed by the methods of the present invention, as will be explained in details further on.

The polypeptide to be contacted with FPP in vitro can be obtained by extraction from any organism expressing it, using standard protein or enzyme extraction technologies. If the host organism is an unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a β-santalene synthase activity, either in an isolated form or together with other proteins, for example in a crude protein extract obtained from cultured cells or microorganisms, may then be suspended in a buffer solution at optimal pH. If adequate, salts, DTT, BSA and other kinds of enzymatic co-factors, may be added in order to optimize enzyme activity. The concentration of these co-factors can be adjusted in order to achieve an optimized yield. For example, lowering the concentration of $Mg^{2+}$ ions in the polypeptide suspension is particularly advantageous to increase the yield of β-santalene. The optimal concentration of $Mg^{2+}$ ions is comprised between 2 and 0.75 mM. Appropriate conditions are described in more details in the Examples further on.

The precursor FPP is added to the polypeptide suspension, which is then incubated at optimal temperature, for example between 15 and 40° C., preferably between 25 and 35° C., more preferably at 30° C. After incubation, the β-santalene produced may be isolated from the incubated solution by standard isolation procedures, such as solvent extraction and distillation, optionally after removal of polypeptides from the solution.

According to another preferred embodiment, the method of any of the above-described embodiments is carried out in vivo. In this case, step a) comprises cultivating a non-human host organism or cell capable of producing FPP and transformed to express at least one polypeptide comprising an amino acid sequence at least 50% identical to SEQ ID NO:1 or 3 and having a β-santalene synthase activity, under conditions conducive to the production of β-santalene.

According to a more preferred embodiment, the method further comprises, prior to step a), transforming a non human organism or cell capable of producing FPP with at least one nucleic acid encoding a polypeptide comprising an amino acid sequence at least 50% identical to SEQ ID NO:1 or 3 and having a β-santalene synthase activity, so that said organism expresses said polypeptide.

According to another preferred embodiment, the method of any of the above-described embodiments is carried out in vivo. In this case, step a) comprises cultivating a non-human host organism or cell capable of producing FPP and transformed to express at least one polypeptide comprising an amino acid sequence at least 60% identical to SEQ ID NO:15 and having a β-santalene synthase activity, under conditions conducive to the production of β-santalene.

According to a more preferred embodiment, the method further comprises, prior to step a), transforming a non human organism or cell capable of producing FPP with at least one nucleic acid encoding a polypeptide comprising an amino acid sequence at least 60% identical to SEQ ID NO:15 and having a β-santalene synthase activity, so that said organism expresses said polypeptide These embodiments of the invention are particularly advantageous since it is possible to carry out the method in vivo without previously isolating the polypeptide. The reaction occurs directly within the organism or cell transformed to express said polypeptide.

According to a particular embodiment of the invention, the at least one nucleic acid encoding the β-santalene synthase comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2, 4 or the complement thereof. According to a more preferred embodiment, said nucleic acid comprises the nucleotide sequence SEQ ID NO:2, 4 or the complement thereof.

In another preferred embodiment, the nucleic acid consists of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2, 4 or the complement thereof. In an even more preferred embodiment, said nucleic acid consists of SEQ ID NO:2, 4 or the complement thereof.

According to a more preferred embodiment the at least one nucleic acid used in any of the above embodiments comprises a nucleotide sequence that has been obtained by modifying SEQ ID NO:2, 3 or the complement thereof. According to an even more preferred embodiment, said at least one nucleic acid consists of a nucleotide sequence that has been obtained by modifying SEQ ID NO:2, 3 or the complement thereof, preferably SEQ ID NO:3 or the complement thereof.

According to a particular embodiment of the invention, the at least one nucleic acid encoding the β-santalene synthase comprises a nucleotide sequence at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:14, 2 or the complement thereof, and preferably to SEQ ID NO:2 or the complement thereof. According to a more preferred embodiment, said nucleic acid comprises the nucleotide sequence SEQ ID NO:14, 2 or the complement thereof, preferably SEQ ID NO:2 or the complement thereof. In an even more preferred embodiment, said nucleic acid consists of SEQ ID NO:14, 2 or the complement thereof, preferably of SEQ ID NO:2 or the complement thereof.

According to a more preferred embodiment the at least one nucleic acid used in any of the above embodiments comprises a nucleotide sequence that has been obtained by modifying SEQ ID NO:14, 2 or the complement thereof. According to an even more preferred embodiment, said at least one nucleic acid consists of a nucleotide sequence that has been obtained by modifying SEQ ID NO:14, 2 or the complement thereof, preferably SEQ ID NO:2 or the complement thereof According to another embodiment, the at least one nucleic acid is isolated from a plant of the *Santalum* species, preferably from *Santalum album*.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the examples.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. Such methods can for example be found in the literature, for example in the following publications: Martin, V. J., Pitera, D. J., Withers, S. T., Newman, J. D., and Keasling, J. D. Nat Biotechnol., 2003, 21(7), 796-802 (transformation of *E. coli*); Wu, S., Schalk, M., Clark, A., Miles, R. B., Coates, R., and Chappell, J., *Nat Biotechnol.*, 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, *Biotechnology and Bioengineering*, 2007, 97(1), 170-181 (transformation of yeast).

To carry out the invention in vivo, the host organism or cell is cultivated under conditions conducive to the production of β-santalene. Accordingly, if the host is a transgenic plant, optimal growth conditions are provided, such as optimal light, water and nutrient conditions, for example. If the host is a unicellular organism, conditions conducive to the production of β-santalene may comprise addition of suitable cofactors to the culture medium of the host. In addition, a culture medium may be selected, so as to maximize β-santalene synthesis. Optimal culture conditions are described in a more detailed manner in the following Examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism used to carry out the method of the invention in vivo is a microorganism. Any microorganism can be used but according to an even more preferred embodiment said microorganism is a bacteria or yeast. Most preferably, said bacteria is *E. coli* and said yeast is *Saccharomyces cerevisiae*.

Some of these organisms do not produce FPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are preferably plant or fungal cells.

According to a preferred embodiment, the at least one polypeptide having a β-santalene synthase activity used in any of the above-described embodiments or encoded by the nucleic acid used in any of the above-described embodiments comprises an amino at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 3. According to a more preferred embodiment, said polypeptide comprises the amino acid sequence SEQ ID NO:1 or 3.

In another preferred embodiment, the polypeptide consists of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 3. In an even more preferred embodiment, said polypeptide consists of SEQ ID NO:1 or 3.

According to another preferred embodiment, the at least one polypeptide having a β-santalene synthase activity used in any of the above-described embodiments or encoded by the nucleic acid used in any of the above-described embodiments an amino acid sequence that is a variant of SEQ ID NO:1 or 3 obtained by genetic engineering, provided that said variant keeps its β-santalene synthase activity, as defined above and has the required percentage of identity to SEQ ID NO:1 or 3. In other terms, said polypeptide preferably comprises an amino acid sequence encoded by a nucleotide sequence that has been obtained by modifying SEQ ID NO:2, 4 or the complement thereof. According to a more preferred embodiment, the at least one polypeptide having a β-santalene synthase activity used in any of the above-described embodiments or encoded by the nucleic acid used in any of the above-described embodiments consists of an amino acid sequence that is a variant of SEQ ID NO:1 or 3 obtained by genetic engineering, i.e. an amino acid sequence encoded by a nucleotide sequence that has been obtained by modifying SEQ ID NO:2, 4 or the complement thereof.

According to another preferred embodiment, the at least one polypeptide having a β-santalene synthase activity used in any of the above-described embodiments or encoded by the nucleic acid used in any of the above-described embodiments is a variant of SEQ ID NO:1 or 3 that can be found naturally in other organisms, such as other plant species, provided that it keeps its β-santalene synthase activity as defined above and has the required percentage of identity to SEQ ID NO:1 or 3.

As used herein, the polypeptide is intended as a polypeptide or peptide fragment that encompasses the amino acid sequences identified herein, as well as truncated or variant polypeptides, provided that they keep their β-santalene synthase activity as defined above and that they share at least the defined percentage of identity with the corresponding fragment of SEQ ID NO:1 or 3.

According to a preferred embodiment, the at least one polypeptide having a (β-santalene synthase activity used in any of the above-described embodiments or encoded by the nucleic acid used in any of the above-described embodiments comprises an amino acid sequence at least 65%, preferably at least 70%, preferably at least 75%, preferably at least 80%, preferably at least 85%, preferably at least 90%, more preferably at least 95% and even more preferably at least 98% identical to SEQ ID NO:15. According to a more preferred embodiment, said polypeptide comprises the amino acid sequence SEQ ID NO:15. In an even more preferred embodiment, said polypeptide consists of SEQ ID NO:15.

According to another preferred embodiment, the at least one polypeptide having a β-santalene synthase activity used in any of the above-described embodiments or encoded by the nucleic acid used in any of the above-described embodiments comprises an amino acid sequence that is a variant of SEQ ID NO:15 obtained by genetic engineering, provided that said variant keeps its β-santalene synthase activity, as defined above and has the required percentage of identity to SEQ ID NO:15. In other terms, said polypeptide comprises an amino acid sequence encoded by a nucleotide sequence that has been obtained by modifying SEQ ID NO:14, 2 or the complement thereof, preferably SEQ ID NO:2 or the complement thereof. According to a more preferred embodiment, the at least one polypeptide having a β-santalene synthase activity used in any of the above-described embodiments or encoded by the nucleic acid used in any of the above-described embodiments consists of an amino acid sequence that is a variant of SEQ ID NO:15 obtained by genetic engineering, i.e. an amino acid sequence encoded by a nucleotide sequence that has been obtained by modifying SEQ ID NO:14, 2 or the complement thereof, preferably SEQ ID NO:2 or the complement thereof.

According to another preferred embodiment, the at least one polypeptide having a β-santalene synthase activity used in any of the above-described embodiments or encoded by the nucleic acid used in any of the above-described embodiments is a variant of SEQ ID NO:15 that can be found naturally in other organisms, such as other plant species, provided that it keeps its β-santalene synthase activity as defined above and has the required percentage of identity to SEQ ID NO:15.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:15

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

According to another embodiment, the at least one polypeptide having a (β-santalene synthase activity used in any of the above-described embodiments or encoded by the nucleic acid used in any of the above-described embodiments is isolated from a plant of the *Santalum* species, preferably from *Santalum album*.

An important tool to carry out the method of the invention is the polypeptide itself. A polypeptide having a β-santalene synthase activity and comprising an amino acid sequence at least 60% identical to SEQ ID NO:15 is therefore another object of the present invention An important tool to carry out the method of the invention is the polypeptide itself. A polypeptide having a β-santalene synthase activity and comprising an amino acid sequence at least 50% identical to SEQ ID NO:1 or 3 is therefore another object of the present invention.

According to a preferred embodiment, the polypeptide is capable of producing a mixture of sesquiterpenes wherein β-santalene represents at least 20%, preferably at least 30%, preferably at least 35%, of the sesquiterpenes produced.

According to a preferred embodiment, the polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 3. According to a more preferred embodiment, the polypeptide comprises the amino acid sequence SEQ ID NO:1 or 3.

According to another preferred embodiment, the polypeptide consists of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 3. According to an even more preferred embodiment, the polypeptide consists of SEQ ID NO:1 or 3.

The at least one polypeptide comprises an amino acid sequence that is a variant of SEQ ID NO:1 or 3, either obtained by genetic engineering or found naturally in Santalum plants or in other plant species. In other terms, when the variant polypeptide is obtained by genetic engineering, said polypeptide comprises an amino acid sequence encoded by a nucleotide sequence that has been obtained by modifying SEQ ID NO:2, 4 or the complement thereof. According to a more preferred embodiment, the at least one polypeptide having a β-santalene synthase activity consists of an amino acid sequence that is a variant of SEQ ID NO:1 or 3 obtained by genetic engineering, i.e. an amino acid sequence encoded by a nucleotide sequence that has been obtained by modifying SEQ ID NO:2, 4 or the complement thereof.

The nucleic acid of the invention can be either present naturally in plants of the *santalum* species or other species, or be obtained by modifying SEQ ID NO:14, 2 or the complement thereof, preferably SEQ ID NO:2 or the complement thereof. Preferably said nucleic acid consists of a nucleotide sequence that has been obtained by modifying SEQ ID NO:14, 2 or the complement thereof, preferably SEQ ID NO:2 or the complement thereof.

The nucleic acids comprising a sequence obtained by mutation of SEQ ID NO:14, 2 or the complement thereof are encompassed by the invention, provided that the sequences they comprise share at least the defined percentage of identity with the corresponding fragments of SEQ ID NO:14, 2 or the complement thereof and provided that they encode a polypeptide having a β-santalene synthase activity, as defined in any of the above embodiments. Preferably, the sequence is obtained by mutation of SEQ ID NO:2 or the complement thereof. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention According to another embodiment, the polypeptide is isolated from a plant of the *Santalum* species, preferably from *Santalum album*.

As used herein, the polypeptide is intended as a polypeptide or peptide fragment that encompasses the amino acid sequence identified herein, as well as truncated or variant polypeptides, provided that they keep their activity as defined above and that they share at least the defined percentage of identity with the corresponding fragment of SEQ ID NO:1 or 3.

The nucleic acid of the invention can be either present naturally in plants of the *santalum* species or other species, or be obtained by modifying SEQ ID NO:14, 2 or the complement thereof, preferably SEQ ID NO:2 or the complement thereof. Preferably said nucleic acid consists of a nucleotide sequence that has been obtained by modifying SEQ ID NO:14, 2 or the complement thereof, preferably SEQ ID NO:2 or the complement thereof.

The nucleic acids comprising a sequence obtained by mutation of SEQ ID NO:14, 2 or the complement thereof are encompassed by the invention, provided that the sequences they comprise share at least the defined percentage of identity with the corresponding fragments of SEQ ID NO:14, 2 or the complement thereof and provided that they encode a polypeptide having a β-santalene synthase activity, as defined in any of the above embodiments. Preferably, the sequence is obtained by mutation of SEQ ID NO:2 or the complement thereof. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein or improve the enzymatic activity of the polypeptide in a to desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as another protein from the terpene biosynthesis pathway, are also encompassed by the polypeptides of the invention. As mentioned above, the nucleic acid encoding the polypeptide of the invention is a useful tool to modify non-human host organisms or cells intended to be used when the method is carried out in vivo.

A nucleic acid encoding a polypeptide according to any of the above-described embodiments is therefore also an object of the present invention.

According to a preferred embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2, 4 or the complement thereof. According to a more preferred embodiment, the nucleic acid comprises the nucleotide sequence SEQ ID NO:2, 4 or the complement thereof.

According to another preferred embodiment, the nucleic acid consists of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2, 4 or the complement thereof. According to an even more preferred embodiment, the nucleic acid consists of SEQ ID NO:2, 4 or the complement thereof.

The nucleic acid of the invention can be either present naturally in plants of the *santalum* species or other species, or be obtained by modifying SEQ ID NO:14, 2 or the complement thereof, preferably SEQ ID NO:2 or the complement thereof. Preferably said nucleic acid consists of a nucleotide sequence that has been obtained by modifying SEQ ID NO:14, 2 or the complement thereof, preferably SEQ ID NO:2 or the complement thereof.

The nucleic acids comprising a sequence obtained by mutation of SEQ ID NO:14, 2 or the complement thereof are encompassed by the invention, provided that the sequences they comprise share at least the defined percentage of identity with the corresponding fragments of SEQ ID NO:14, 2 or the complement thereof and provided that they encode a polypeptide having a β-santalene synthase activity, as defined in any of the above embodiments. Preferably, the sequence is obtained by mutation of SEQ ID NO:2 or the complement thereof. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention According to another embodiment, the nucleic acid is isolated from a plant of the *Santalum* species, preferably from *Santalum album*.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

The nucleic acid of the invention can be either present naturally in plants of the *santalum* species or other species, or be obtained by modifying SEQ ID NO:2, 4 or the complement thereof. Preferably said nucleic acid consists of a nucleotide sequence that has been obtained by modifying SEQ ID NO:2, 4 or the complement thereof.

The nucleic acids comprising a sequence obtained by mutation of SEQ ID NO:2, 4 or the complement thereof are encompassed by the invention, provided that the sequences they comprise share at least the defined percentage of identity with the corresponding fragments of SEQ ID NO:2, 4 or the complement thereof and provided that they encode a polypeptide having a β-santalene synthase activity, as defined in any of the above embodiments. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

The nucleic acid of the invention can be either present naturally in plants of the *santalum* species or other species, or be obtained by modifying SEQ ID NO:14, 2 or the complement thereof, preferably SEQ ID NO:2 or the complement thereof. Preferably said nucleic acid consists of a nucleotide sequence that has been obtained by modifying SEQ ID NO:14, 2 or the complement thereof, preferably SEQ ID NO:2 or the complement thereof.

The nucleic acids comprising a sequence obtained by mutation of SEQ ID NO:14, 2 or the complement thereof are encompassed by the invention, provided that the sequences they comprise share at least the defined percentage of identity with the corresponding fragments of SEQ ID NO:14, 2 or the complement thereof and provided that they encode a polypeptide having a β-santalene synthase activity, as defined in any of the above embodiments. Preferably, the sequence is obtained by mutation of SEQ ID NO:2 or the complement thereof. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention Another important tool for transforming host organisms or cells suitable to carry out the method of the invention in vivo is an expression vector comprising a nucleic acid according to any embodiment of the invention. Such a vector is therefore also an object of to the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for making polypeptides having a β-santalene synthase activity, as disclosed further below.

Recombinant non-human host organisms and cells transformed to harbor at least one nucleic acid of the invention so that it heterologously expresses or over-expresses at least one polypeptide of the invention are also very useful tools to carry out the method of the invention. Such non-human host organisms and cells are therefore another object of the present invention.

A nucleic acid according to any of the above-described embodiments can be used to transform the non-human host organisms and cells and the expressed polypeptide can be any of the above-described polypeptides.

Non-human host organisms of the invention may be any non-human multicellular or unicellular organisms. In a preferred embodiment, the non-human host organism is a plant, a prokaryote or a fungus. Any plant, prokaryote or fungus is suitable to be transformed according to the present invention. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism is a microorganism. Any microorganism is suitable for the present invention, but according to an even more preferred embodiment said microorganism is a bacteria or yeast. Most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells or fungal cells.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual,* 1985, Elsevier, New York and Sambrook et al., *Molecular Cloning: A Laboratory Manual,* 2$^{nd}$ edition, 1989, Cold Spring Harbor Laboratory Press. Cloning and expression vectors for higher plants and/or plant cells in particular are available to the skilled person. See for example Schardl et al. *Gene* 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection. In order to carry out the method for producing β-santalene in vitro, as exposed herein above, it is very advantageous to provide a method of making at least one polypeptide having a β-santalene synthase activity as described in any embodiment of the invention. Therefore, the invention provides a method for producing at least one polypeptide according to any embodiment of the invention comprising a) culturing a non-human host organism or cell transformed with the expression vector of the invention, so that it harbors a nucleic acid according to the invention and expresses or over-expresses a polypeptide of the invention;

b) isolating the polypeptide from the non-human host organism or cell cultured in step a).

According to a preferred embodiment, said method further comprises, prior to step a), transforming a non-human host organism or cell with the expression vector of the invention, so that it harbors a nucleic acid according to the invention and expresses or over-expresses the polypeptide of the invention.

A nucleic acid according to any of the above-described embodiments can be used.

Transforming and culturing of the non-human host organism or cell can be carried out as described above for the method of producing β-santalene in vivo. Step b) may be performed using any technique well known in the art to isolate a particular polypeptide from an organism or cell.

A "polypeptide variant" as referred to herein means a polypeptide having a β-santalene synthase activity and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, *Biochemistry,* 1983, Addison-Wesley Pub. Co. The effects of such substitutions can be calculated using substitution score matrices such a PAM-120, PAM-200, and PAM-250 as discussed in Altschul, *J. Mol. Biol.,* 1991, 219, 555-565. Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acid from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, for examples plants from the *Santalum* species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Fusion polypeptide encompassed by the invention also comprise fusion polypeptides resulting from a fusion of other functional proteins, such as other proteins from the terpene biosynthesis pathway.

Therefore, in an embodiment, the present invention provides a method for preparing a variant polypeptide having a β-santalene synthase activity, as described in any of the above embodiments, and comprising the steps of:

(a) selecting a nucleic acid according to any of the embodiments exposed above;
(b) modifying the selected nucleic acid to obtain at least one mutant nucleic acid;
(c) transforming host cells or unicellular organisms with the mutant nucleic acid sequence to express a polypeptide encoded by the mutant nucleic acid sequence;
(d) screening the polypeptide for at least one modified property; and,
(e) optionally, if the polypeptide has no desired variant β-santalene synthase activity, repeating the process steps (a) to (d) until a polypeptide with a desired variant β-santalene synthase activity is obtained;
(f) optionally, if a polypeptide having a desired variant β-santalene synthase activity was identified in step (d), isolating the corresponding mutant nucleic acid obtained in step (c).

According to a preferred embodiment, the variant polypeptide prepared is capable of producing a mixture of sesquiterpenes wherein β-santalene represents at least 20%, preferably at least 30%, preferably at least 35% of the sesquiterpenes produced.

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. *Proc Natl Acad Sci USA.*, 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, the polypeptide comprising SEQ ID NO:1 may be recombined with any other sesquiterpene synthase encoding nucleic acids, for example isolated from an organism other than *Santalum album*. Thus, mutant nucleic acids may be obtained and separated, which may be used for transforming a host cell according to standard procedures, for example such as disclosed in the present examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{MAX}$ value, modified regio-chemistry or stereochemistry and altered substrate utilization or product distribution. The screening of enzymatic activity can be performed according to procedures familiar to the skilled person and those disclosed in the present examples. Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

All the publications mentioned in this application are incorporated by reference to disclose and describe the methods and/or materials in connection with which the publications are cited.

DESCRIPTION OF THE DRAWINGS

FIGS. 1A-1F: GC-MS analyses of the sesquiterpene produced by the recombinant santalene synthase from *Santalum album* (SaSantS), wherein:

FIG. 1A: Total ion chromatogram. 1, α-santalene; 2, trans-α-bergamotene; 3, epi-β-santalene; 4, β-santalene; 5, β-farnesene FIGS. 1B-1F: Mass spectra of the peaks identified as sesquiterpenes.

SPECIFIC EMBODIMENTS OF THE INVENTION OR EXAMPLES

Figure 1A:
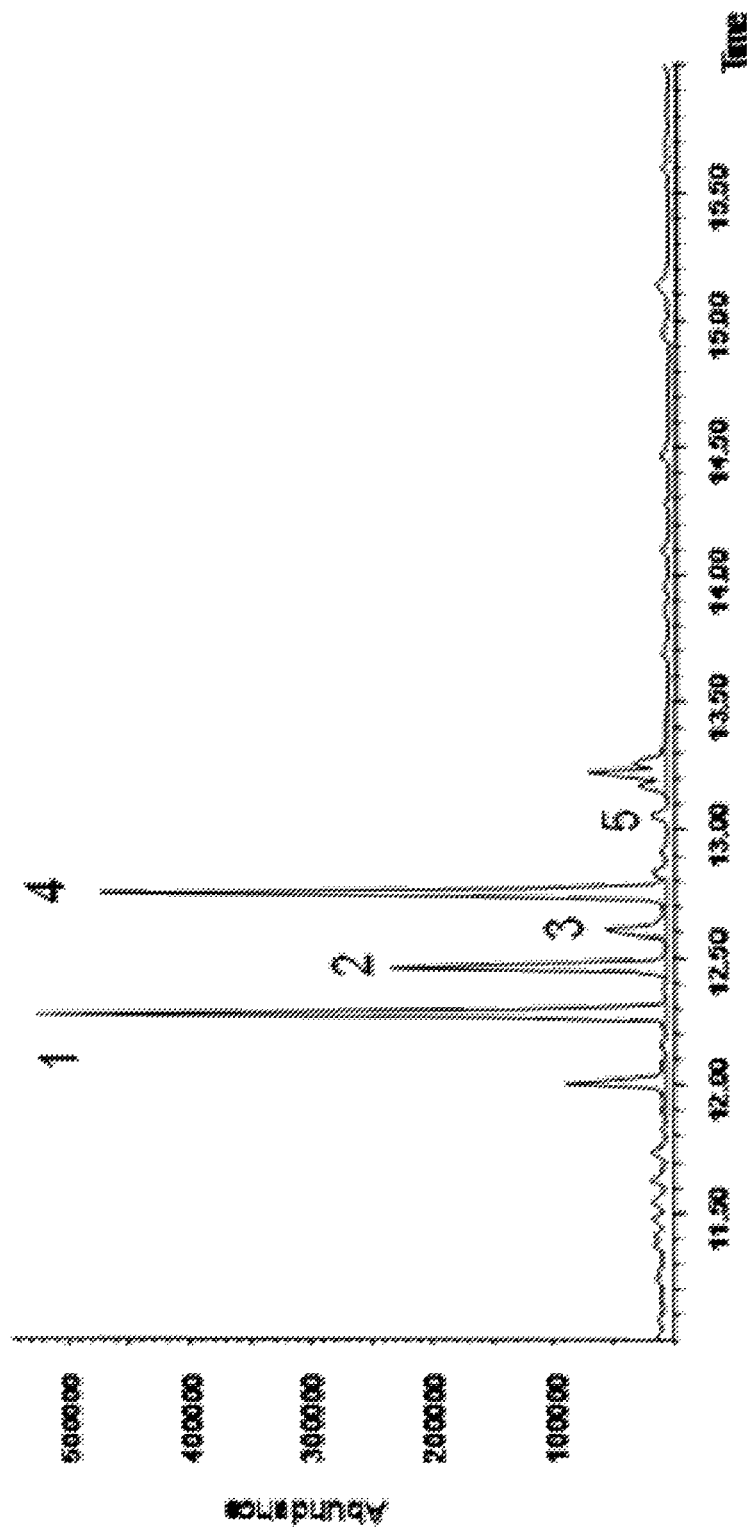

The invention will now be described in further detail by way of the following Examples.

Example 1

DNA Library Construction, Sequencing and Extraction of Terpene Synthase Related Sequences Young hypocotyls segments obtained from aseptically germinated seeds of *Santalum album* L. (5 weeks old) were used to induce callus formation. The seeds of *S. album* were obtained from B&T World Seeds (Aigues-Vives, France) and from Sandeman Seeds (Lalongue, France). The seeds were first surface sterilised in 2.5% HClO for 120 minutes, and rinsed three times in sterile ultrapure water. The seeds were then shelled and placed on MS basal medium (Murashige & Skoog, 1962, *Physiologia Plantarum* 15, 473-497) supplemented with 15 g/L sucrose and 7.8 g/L agar, pH 5.7. Germination was typically observed after 9 to 18 days with a yield of approximately 40%. The plantlets were allowed to grow in-vitro for 2 to 3 months in a cultivation room at a temperature of 27° C., with cool, white fluorescent light and with a 16 hours photoperiod. To induce the formation of green callus, the hypocotyls segments were cut into 3-4 mm transverse segments which were placed on Gbg basal medium (Gamborg & al, 1968, *Exp Cell Res.* 50(1), 151-158) supplemented with 0.5 µM 2,4D (2,4-Dichlorophenoxyacetic acid, Sigma-Aldrich Co.) and 10 µM Kin (Kinetin, Sigma-Aldrich Co.) in Petri dishes. The growth of the callus was perpetuated by transferring the tissue every four weeks to fresh medium in Petri dishes. All callus cultures were performed in a growth chamber in the same conditions as above.

Callus obtained after one month of culture in Gbg medium containing 5 µM Kin and 2 mM ACC were used for the RNA extraction and cDNA library construction. Total RNA were extracted following the protocol described by Lefort and Douglas (Ann. For. Sci. 56 (1999), 259-263) except that the RNase treatment was omitted. The pellet was resuspended in 200 µl RNase-free water and centrifuged twice for 10 minutes at 20000 g to remove the polysaccharides. Approximately 125 µg total RNA were obtained from 2.2 g of cells. The mRNAs were purified using the FastTrack® 2.0 mRNA Isolation Kit (Invitrogen) and a cDNA library was made using the SMART® PCR cDNA Synthesis Kit (Clontech Laboratories, Inc.) following the manufacturer's instructions.

The technology of massive parallel sequencing of small DNA fragments developed by Illumina (San Diego, Calif.) was used to sequence the whole cDNA library. The preparation of the DNA for sequencing, the sequencing and the assembling of the reads were performed by Fasteris SA (Plan-les-Ouates, Switzerland). The cDNA library was treated following the Genomic Sample Prep Kit (Illumina) and sequenced on the Genome Analyzer system (Illumina). A total of 4.03 millions of 35 bp sequences (reads) were obtained. These reads were assembled using EDENA 2.1.1, a software finding overlaps between the reads and assembling de novo contigs (Hernandez et al, De novo bacterial genome sequencing: Millions of very short reads assembled on a desktop computer. *Genome Res.* 2008; 18:802-809). The assembling was run with minimum matches of 26 to 20 bases. After eliminating contigs shorter than 100 bases, 1983 to 3473 unique contigs were obtained with a maximum length of 1331 to 1914 depending of the parameters selected for the assembling. Another assembling was performed using the Velvet 1.0 program (Zerbino and Birney (2008), Velvet: algorithms for de novo short read assembly using de Bruijn graphs. *Genome Res.* 18(5), 821-829), providing 5905 unique contigs of length between 100 and 1616 bases.

All the contigs generated were compared against a protein sequences data base (non-redundant protein sequences, NCBI, http://www.ncbi.nlm.nih.gov) using the Blastx algorithm (Altschul et al, *J. Mol. Biol.* 215, 403-410, 1990; http://www.ncbi.nlm.nih.gov/blast/Blast.cgi). The contigs showing significant sequence homology with plant sesquiterpene synthases were retained. A total of 46 contigs with a length of 100 to 621 bases were thus selected. These contigs were then processed using the CAP program (Huang, *Genomics* 14(1), 18-25, 1992) to assemble them and generate longer sequences. Five unique contigs of length of 445 to 1064 were thus assembled. The deduced amino acid sequences showed significant homology with plant terpene synthases and especially with sequences described or annotated as monoterpene synthases. Alignment of these amino acid sequences showed that at least two distinct cDNAs were present (two sequences were found in most of the positions across the alignment). This alignment showed also that at least one N-terminal and one C-terminal sequence was present. To obtain the full length sequences and to assign the exact 5'-end and 3'-end sequences to each cDNA, a rapid amplification of cDNA ends experiment (RACE) was employed.

Example 2

Amplification of the Full-Length Sequences of a Terpene Synthase cDNA

For the RACE experiments, a set of primers was designed from one out of the five contigs obtained as described above. Thus the forward primers SCH5-Ct58-R1 (SEQ ID NO:6) and SCH5-Ct58-R2 (SEQ ID NO:7) and the reverse primers SCH5-Ct58-F3 (SEQ ID NO:8) and SCH5-Ct58-F4 (SEQ ID NO:9) were deduced from SCH5-contig-5 (SEQ ID NO:5).

The PCR were performed with the Universal Primer A Mix (UPM) (SMART™ RACE cDNA Amplification Kit, Clontech Laboratories, Inc.) in 50 µl final volume containing 200 µM dNTPs mix, 5 µl cDNA library (Example 1), 0.2 µM gene-specific primer, 0.2 µM UPM Primer Mix (Clontech Laboratories, Inc.), 1 µl Advantage 2 Polymerase Mix (Clontech Laboratories, Inc.) and 5 µl 10× cDNA PCR Reaction Buffer (Clontech Laboratories, Inc.). The thermal cycling conditions were as follows: 3 minutes at 94° C.; 5 cycles of 30 sec at 94° C. and 3 minutes at 72° C.; 5 cycles of 30 sec at 94° C. and 3 minutes at 70° C.; 5 cycles of 30 sec at 94° C. and 3 minutes at 68° C.; 3 minutes at 72° C. With the 5'RACE, a 610 bp DNA fragment (SCH5-Ct58 RR1, SEQ ID NO:10) including the 5'end of the cDNA was obtained. With the 3'RACE a 1049 bp fragment (SCH5-Ct58-RF4, SEQ ID NO:11) was obtained and the combination of the two RACE products with the SCH5-contig-5 sequence (SEQ ID NO:5) allowed the reconstitution of a new full-length cDNA (SCH5-Ct58, SEQ ID NO:12). The 2157 bp SCH5-Ct58 cDNA encoded for a 569 amino acid protein (SEQ ID NO:13) showing homology with plant terpene synthases sequences and containing motifs characteristic of terpene synthases such as the DDxxD motif present in all monoterpene and sesquiterpene synthases. Interestingly the amino acid sequence showed higher similarity to monoterpene synthases than to sesquiterpene synthases. However the presence of chloroplast peptide signal, a common feature in plant monoterpene synthases, was not predicted from the analysis of the N-terminal sequence (Emanuelsson, O., Nielsen, N., and von Heijne, G. 1999.

ChloroP, a neural network-based method for predicting chloroplast transit peptides and their cleavage sites. Protein Science 8, 978-984).

Example 3

Heterologous Expression and In-Vitro Enzymatic Activity of SCH5-Ct58

We decided to modify the DNA sequence of SCH5-Ct58 (SEQ ID NO:12) and to redesign the sequence for optimal heterologous expression in *E coli* cells. To start with the true amino acid sequence, the exact nucleotidic sequence of SCH5-Ct58 in the cDNA library had first to be established. The Eland Software (Illumina) was used to retrieve all reads matching with the SCH5-Ct58 sequence (SEQ ID NO:12) with a maximum of 2 mismatches. A total of 5224 reads were recovered and were aligned using the CAP program (Huang, Genomics 14(1), 18-25, 1992) with the SCH5-Ct58 DNA sequence (SEQ ID NO:12) as a reference. The average coverage over the whole sequence was above 100× allowing for the unambiguous deduction of the new cDNA sequence SCH5-Ct94 (SEQ ID NO:14). In this new sequence 5 bases were corrected compared to the SCH5-Ct58 sequence (SEQ ID NO:12) deduced from the RACE results and those corrections resulted in a new amino acid sequence (SCH5-Ct94, SEQ ID NO:15) with a two-residues difference. For heterologous expression, the DNA sequence of SCH5-Ct94 (SEQ ID NO:14) was modified to remove the first 23 codons and replace by the ATGGCT sequence and the codon usage was changed to optimize the sequence for *E coli* expression (DNA 2.0, Menlo Park, Calif., USA). The cDNA thus designed (SCH5-Ct94-opt, SEQ ID NO:2) was synthesized (DNA 2.0, Menlo Park, Calif., USA) and sub-cloned into the NdeI-KpnI sites of the pETDuet-1 plasmid providing the plasmid Ct94-pETDuet. This optimized cDNA sequence encoded for the polypeptide SCH5-Ct94-opt (SEQ ID NO:1).

Figure 1B:
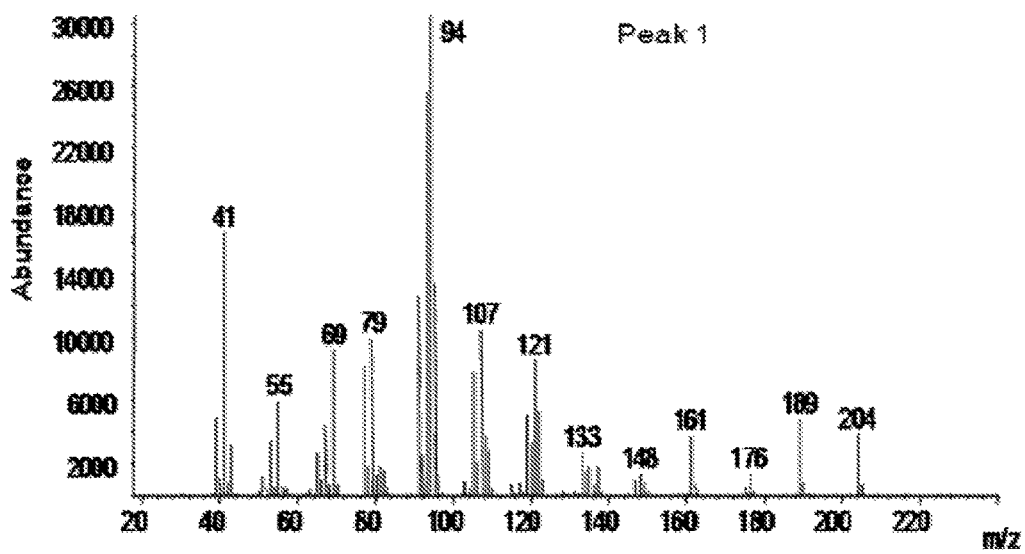
Figure 1C:
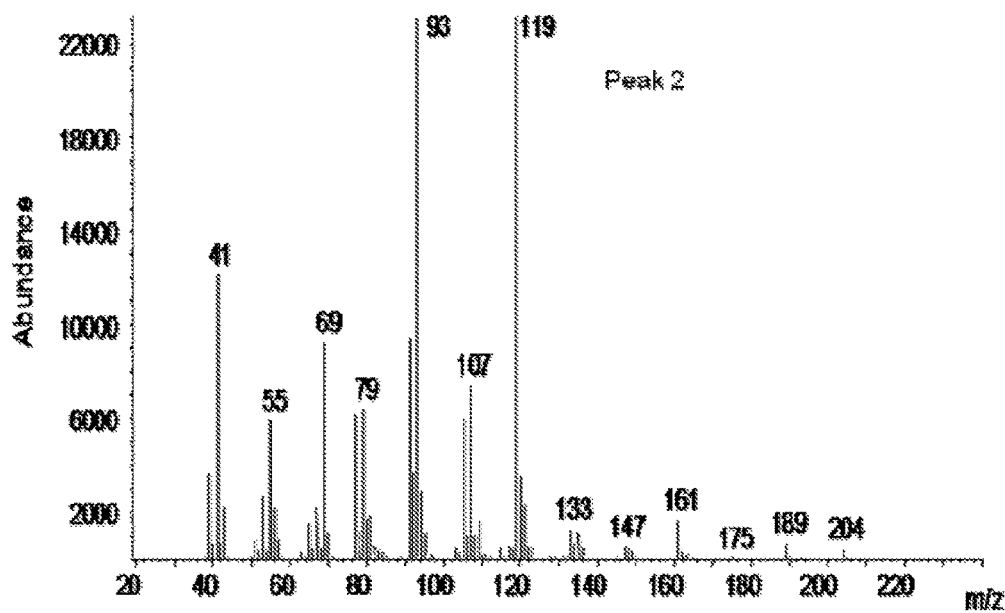
Figure 1D:
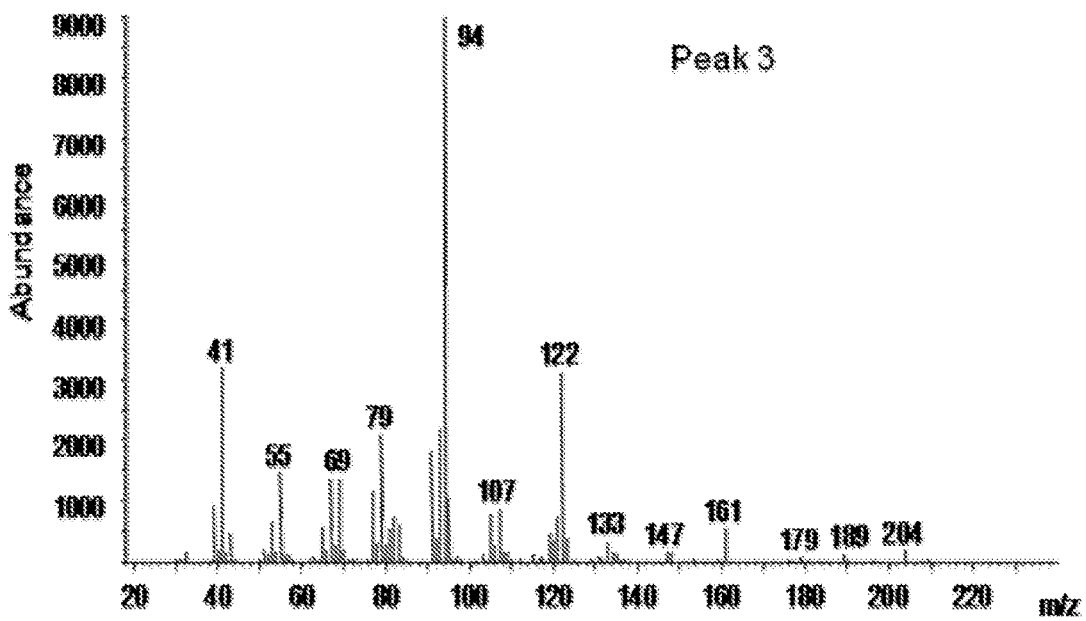
Figure 1E:
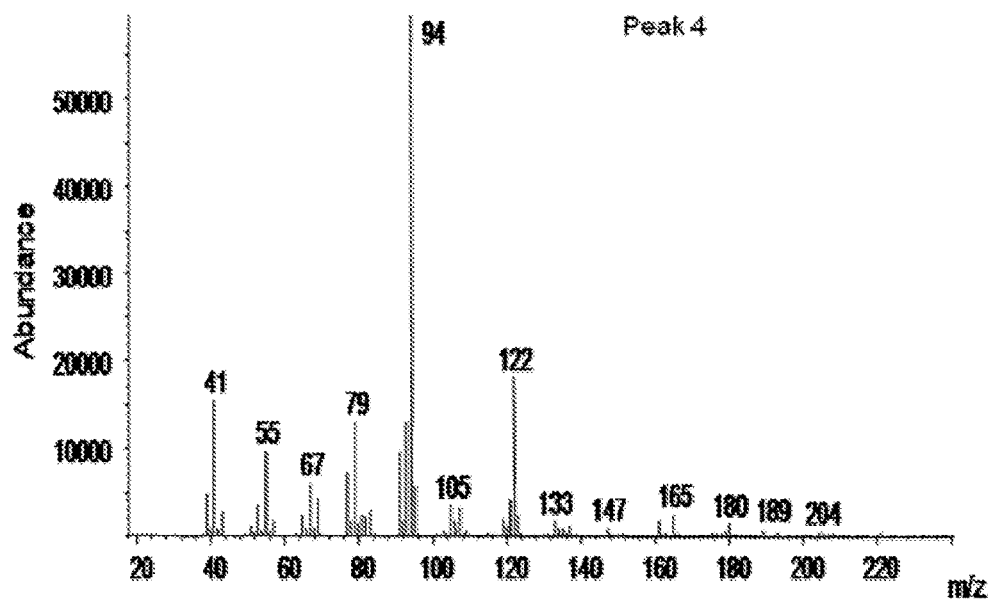
Figure 1F:
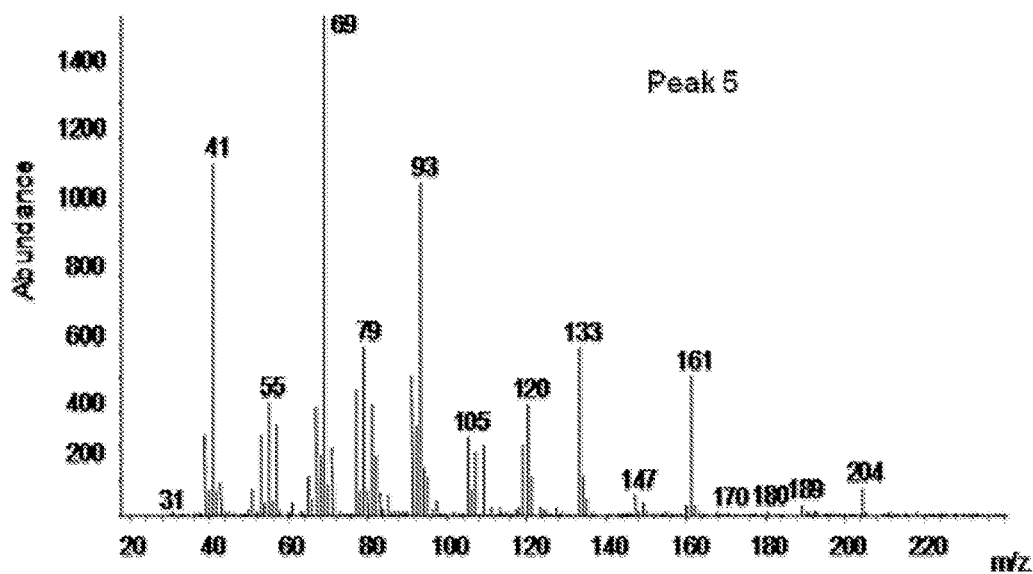
Figure 2A:
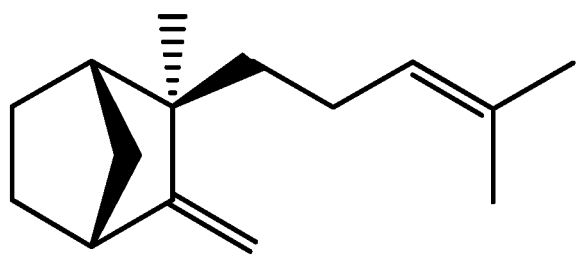
FIGS. 2A-B: Molecular structure of β-santalene and β-santalol.
Figure 2B:
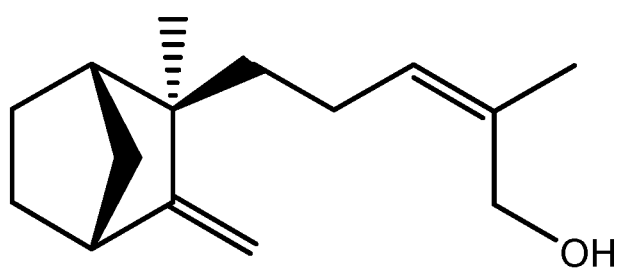

Heterologous expression of Ct94 was performed in *E coli* BL21(DE3) cells using the plasmid Ct94-pETDuet. In-vitro enzyme assays were performed with FPP as substrate in the conditions described above and sesquiterpene synthase activity was observed with formation of a mixture of five sesquiterpenes. The identity of these sesquiterpenes was confirmed by GC-MS as being the sesquiterpene characteristic of *santalum album*: α-santalene, trans-α-bergamotene, epi-β-santalene, β-santalene and β-famesene (FIG. 1). At pH 7.0 and in the presence of 15 mM $MgCl_2$, the relative proportion of the recombinant sequiterpene products was 38.0% of α-santalene, 18.2% of trans-α-bergamotene, 5.7% of epi-β-santalene, 36.7% of β-santalene and 1.3% of β-famesene. Thus the SCH-Ct98-opt cDNA encoded for a β-santalene synthase. The ratio of the products was very similar to the proportion observed in *Santalum album* oil for the hydroxylated products of these sesquiterpenes. No activity was detected when $MgCl_2$ was omitted and the medium supplemented with 2.5 mM EDTA (to chelate residual cations) showing the strict requirement for divalent cations. The nature and concentration of the divalent cation present in the assay had an effect on the product profile (Table 1). For instance, lowering the concentration of $Mg^{2+}$ had a benefit effect for β-santalene, the latest becoming the major product of the enzyme. Moreover, the addition of $Mn^{2+}$ had a negative effect on the formation of β-santalene since the proportion of the santalene sesquiterpene products decreased and the proportion of trans-α-bergamotene and β-farnesene increased, trans-α-bergamotene being the major product of the enzyme in the presence of 1 mM $MgCl_2$.

TABLE 1

Effect of the concentration of $Mg^{2+}$ and $Mn^{2+}$ ions on the composition of the mixture of sesquiterpenes obtained by contacting SEQ ID NO: 1 with FPP

| | Percentage, relative to the whole product mixture | | | |
|---|---|---|---|---|
| | 15 mM $MgCl_2$ | 2 mM $MgCl_2$ | 0.75 mM $MgCl_2$ | 0.75 mM $MgCl_2$ + 1 mM $MnCl_2$ |
| α-santalene | 38.0 | 33.0 | 36.5 | 24.5 |
| trans-α-bergamotene | 18.2 | 11.8 | 12.6 | 35.4 |
| epi-β-santalene | 5.7 | 6.4 | 5.6 | 4.1 |
| β-santalene | 36.7 | 47.5 | 44.1 | 33.3 |
| β-farnesene | 1.3 | 1.3 | 1.1 | 2.75 |

Example 4

In-Vivo Production of Sesquiterpenes in *E coli* Using the Ct94 cDNA

The use of the *S. album* santalene synthase for the in-vivo production of sesquiterpenes in *E coli* cells was evaluated by coexpressing the enzymes of a five step biosynthetic pathway converting mevalonic acid to FPP.

The yeast FPP synthase gene was amplified from *S. cerevisiae* genomic DNA using the primers FPPy_NcoI (SEQ ID NO:16) AND fppY-Eco (SEQ ID NO:17). The amplified DNA was ligated as NdeI-EcoRI fragment in the first multi cloning site (MCS1) of the pACYCDuet-1 plasmid providing the plasmid FPPs-pACYCDuet harbouring the FPPs gene under the control of the T7 promoter. An operon including the genes encoding for a mevalonate kinase (mvaK1), a phosphomevalonate kinase (mvaK2), a mevalonate diphosphate decarboxylase (MvaD) and a isopentenyl diphospahte isomerase (idi) was amplified from genomic DNA of *Streptococcus pneumoniae* (ATCC BAA-334) with the primers MVA-up1-start (SEQ ID NO:18) and MVA-up2-stop (SEQ ID NO:19). The PCR was performed using the PfuUltra™ II Fusion HS DNA polymerase (Stratagen). The composition of the PCR mix was according to the manufacturer instructions. The thermal cycling condition were 2 minutes at 95° C.; 30 cycles of 20 sec at 95° C., 20 sec at 58° C. and 90 sec at 72° C.; and 3 minutes at 72° C. The 3.8 Kb fragment was purified on an agarose gel and ligated using the In-Fusion™ Dry-Down PCR Cloning Kit (clontech) into the second MCS of the FPPs-pACYCDuet plasmid digested with NdeI and XhoI providing the plasmid pACYCDuet-4506. The sequences of the two inserts were fully sequenced to exclude any mutation.

BL21 Star™ (DE3) *E. coli* cells (Invitrogen) were co-transformed with the plasmids pACYCDuet-4506 and Ct94-pETDuet and transformed cells were selected on carbenicillin (50 µg/ml) chloramphenicol (34 µg/ml) LB-agarose plates. Single colonies were used to inoculate 5 mL LB medium with 50 µg/ml carbenicilin and 34 µg/ml chloramphenicol. The culture was incubated overnight at 37° C. The next day 2 mL of TB medium supplemented with the same antibiotics were inoculated with 0.2 mL of the overnight culture. After 6 hours incubation at 37° C., the culture was cooled down to 28° C. and 1 mM IPTG, 2 mg/mL mevalonate (prepared by dissolving mevalonolactone (Sigma) in 0.5 N NaOH at a concentration of 1 g/mL and incubating the solution for 30 minutes at 37° C.) and 0.2 mL decane were added to each tube. The cultures were incubated for 48 hours at 28° C. The cultures were then extracted twice with 2 volumes of ethyl acetate, the organic phase was concentrated to 500 μL and analyzed by GC-MS as described above in Example 3. In these conditions sesquiterpene production above 200 mg/L was routinely achieved. Beta-santalene was produced.

Example 5

In-Vivo Production of Sesquiterpenes in *S. cerevisiae* Using the Ct94 cDNA

For in-vivo production of sesquiterpenes in yeast cells, a *saccharomyces cerevisiae* strain YNP5 in which the ERG9 gene (coding for the squalene synthase, the enzyme converting FPP to squalene) has been down-regulated by replacing the native ERG9 promoter with the regulable MET3 promoter. In previous work with plant sesquiterpene synthases, this strategy led to a reduced ergosterol biosynthesis in the cells and an accumulation of FPP available for sesquiterpene synthases (Asadollahi, *Biotechnology and Bioengineering*, 99(3), 666-677, 2008).

The SCH5-Ct94-opt cDNA (SEQ ID NO:2) was amplified from the Ct94-pETDuet with the primers Ct94_BamHI (SEQ ID NO:20) and T7term (SEQ ID NO:21). The PCR was performed with the Pfu DNA Polymerase (Promega) using the following thermal cycling condition: 90 sec at 94° C.; 35 cycles of 45 sec at 94° C., 45 sec at 55° C., 4 minutes at 72° C.; and 10 minutes at 72° C. The amplified cDNA was digested with the BamHI and XhoI restriction sites and ligated in the corresponding sites of the pESC-URA plasmid (Stratagen) providing the plasmid Ct94-pESC-ura. S.c. The YNP5 cells were transformed using the S.c. EasyComp™ Transformation Kit (Invitrogen).

One single colony of transformed yeast strains were used to inciluate 20 ml of YNB medium (5 g/L (NH$_4$)$_2$SO$_4$; 3 g/L KH$_2$PO$_4$; 0.5 g/L MgSO$_4$. 7 H$_2$O; 1 mL/L trace metal solution) supplemented with 2% glucose. The culture was incubated for 24 hours at 28° C. The cells were recovered by centrifugation and resuspended in 20 mL of YNB medium supplemented with 2% galacoste. After on 1 hour culture, methionine at 0.5 mM final concentration and 2 mL decane were added to the culture. After 24 hours incubation at 28° C., the cultures were extracted with ethyl acetate and analysed by GC-MS as described in Example 4. The total quantity of sesquiterpenes produced by the yeast cells in these conditions was estimated at 50 mg/L.

Example 6

Isolation of a Santalene Synthase from *Santalum Album* Roots

Seedlings of *Santalum album* obtained from aseptically germinated seeds were transferred to soil 5 to 10 weeks after germination. Since *santalum* species are root hemiparasites, the soil adaptation was made in close contact with 6-months to 1-year old citrus (*Citrus sinensis*) plants. The roots of the *santalum plants* were harvested, 2-3 years after the transfer to the soils and separated from the host plant roots. GC-MS analysis of an extract of these roots showed the presence of the sandalwood oil characteristic sesquiterpenes. Total RNA was extracted from the roots using the Concert™ Plant RNA Reagent (Invitrogen). From 12 g of tissue, 640 μg of total RNA were isolated. The mRNA were purified using the FastTrack® 2.0 mRNA Isolation Kit (Invitrogen) and a cDNA library was made using the Marathon™ cDNA Amplification Kit (Clontech Laboratories, Inc.) following the manufacturer instructions.

An amount of 1 μg of cDNA was used for sequencing using the Genome Analyzer System (Illumina). A total of 10.3 millions of 35 bp-length reads were obtained. These reads were assembled using in parallel the Edena (Hernandez et al, 2008, *Genome Res.* 18, 802-809) and the Velvet (Zerbinoa and Birney, 2008, *Genome Res.* 18: 821-829) assembler softwares resulting in 18'937 and 22'414 unique contigs with an average range of 242 and 211 bp. The reads were searched using the tBlastn program (Altschul et al, 1990, *J. Mol. Biol.* 215, 403-410) with the SCH5-CT94 amino acid sequence (SEQ ID NO:15) as query sequence. Fifteen contigs were selected showing significant homology of their deduced amino acid sequences with plant sesquiterpene synthases. These selected contigs were reassembled into two distinct sequences, of which SCH10-Ct8201 (SEQ ID NO:22) was 383 bp in length and showed the highest homology with SCH5-CT94 DNA sequence (SEQ ID NO:14). The forward primer SCH10-Ctg8201-F2 (SEQ ID NO:23) was designed from the SCH10-Ct8201 sequence and successfully used for 3'RACE using the Marathon™ cDNA Amplification Kit (Clontech Laboratories, Inc.). From the sequence of the 3'RACE product thus obtained, two reverse primers (SCH10-Ct19779-R3 (SEQ ID NO:24) and SCH10-Ct19779-R4 (SEQ ID NO:25)) were designed and successfully used for the amplification by 5'RACE of the 5'end of the corresponding cDNA. From the sequences of the 3'RACE and 5'RACE a full-length sequence of a new terpene synthase was thus reconstituted. In order to verify the sequence, the MAQ program (Li et al, 2008, *Genome Res.* 18(11), 1851-1858) was used to search and map all the reads with a maximum of 2 mismatches. This approach provided a 1725 bp-length DNA sequence (SEQ ID NO:26) encoding for a 570 amino acid-length protein (SEQ ID NO:27) having 91.9% identity with the amino acid sequence of SCH5-Ct94 (SEQ ID NO:15).

For heterologous expression in *E coli*, an optimized cDNA was designed by deleting the 21 first codons, adding the sequence ATGGCTACC as the first 3 codons and optimizing the codon usage for *E coli*. This optimized sequence (SCH10-Ct8201-opt, SEQ ID NO:4) encoding for the N-terminal modified protein SCH10-Tps8201-opt (SEQ ID NO:3) was synthesized (DNA 2.0; Menlo Park, Calif., USA) and sub-cloned in the NdeI-KpnI sites of the pETDuet-1 expression plasmid (Novagen). Heterologous expression and enzymatic characterization of SCH10-Tps8201-opt (SEQ ID NO:3) was performed as described in Example 3. The recombinant protein showed sesquiterpene synthase activity and produced from FPP the same mixture of sesquiterpenes as the SCH5-CT94-opt recombinant protein (SEQ ID NO:1, Example 3) with the same relative proportions.

What is claimed is:

1. An isolated nucleic acid molecule comprising
   a) the cDNA sequence of SEQ ID NO: 14 or the full-length complement thereof;
   b) a modified sequence of SEQ ID NO: 14, wherein the first 23 codons of SEQ ID NO: 14 were removed; or
   c) the modified sequence of b) optimized for *E. coli* expression.

2. An expression vector comprising
   a) the nucleic acid molecule of claim 1;
   b) a nucleic acid encoding a polypeptide comprising an amino acid sequence having at least 90% sequence identity to SEQ ID NO: 1, SEQ ID NO: 3, SEQ ID NO: 15, or SEQ ID NO: 27 and having a β-santalene synthase activity; or
   c) the nucleic acid of b) comprising a nucleotide sequence at least 90% identical to SEQ ID NO: 2, SEQ ID NO: 4, SEQ ID NO: 14, SEQ ID NO: 26, wherein the nucleic acid encodes a polypeptide having a β-santalene synthase activity; or
   d) the nucleic acid sequence of SEQ ID NO: 2, SEQ ID NO: 4, SEQ ID NO: 14, SEQ ID NO: 26 or the full-length complement thereof.

3. A non-human host organism or cell
   a) transformed to harbor
      i) the nucleic acid of claim 1;
      ii) a nucleic acid encoding a polypeptide having a β-santalene synthase activity comprising an amino acid sequence having at least 90% sequence identity to SEQ ID NO: 1, SEQ ID NO: 3, SEQ ID NO: 15, or SEQ ID NO: 27; or
      iii) the nucleic acid of ii) comprising a nucleotide sequence having at least 90% sequence identity to SEQ ID NO: 2, SEQ ID NO: 4, SEQ ID NO: 14, SEQ ID NO: 26, wherein the nucleic acid encodes a polypeptide having a β-santalene synthase activity; or
      iv) the nucleic acid sequence of SEQ ID NO: 2, SEQ ID NO: 4, SEQ ID NO: 14, SEQ ID NO: 26 or the full-length complement thereof; or
   b) comprising an expression vector comprising the nucleic acid of i), ii), iii) or iv) above;
   so that the non-human host organism or cell heterologously expresses or over-expresses at least one polypeptide having a β-santalene synthase activity.

4. The non-human host organism or cell of claim 3, wherein said non-human host organism or cell is a plant, a prokaryote, a fungus, a plant cell, or a fungal cell.

5. The non-human host organism or cell of claim 3, wherein said non-human host organism is a microorganism.

6. The non-human host organism of claim 5, wherein said microorganism is a bacteria or yeast.

7. The non-human host organism of claim 6, wherein the bacteria is *E. coli* and the yeast is *Saccharomyces cerevisiae*.

8. The non-human organism or cell of claim 3, wherein the non-human organism or cell comprises
   a) a nucleic acid encoding a polypeptide having a β-santalene synthase activity comprising an amino acid sequence having at least 95%, 98% or 100% sequence identity to SEQ ID NO: 1, SEQ ID NO: 3, SEQ ID NO: 15, or SEQ ID NO: 27; or
   b) a nucleic acid comprising the nucleotide sequence of SEQ ID NO: 2, SEQ ID NO: 4, SEQ ID NO: 14, SEQ ID NO: 26 or the full-length complement thereof.

9. The expression vector of claim 2, wherein the expression vector comprises
   a) a nucleic acid encoding a polypeptide having a β-santalene synthase activity comprising an amino acid sequence having at least 95%, 98% or 100% sequence identity to SEQ ID NO: 1, SEQ ID NO: 3, SEQ ID NO: 15, or SEQ ID NO: 27; or
   b) a nucleic acid comprising the nucleotide sequence of SEQ ID NO: 2, SEQ ID NO: 4, SEQ ID NO: 14, SEQ ID NO: 26 or the full-length complement thereof.

10. The non-human organism or cell of claim 3, wherein the non-human organism or cell is capable of producing farnesyl pyrophosphate (FPP).

11. A method for producing β-santalene comprising
    a) cultivating the non-human organism or cell of claim 10 under conditions conducive to the production of β-santalene; and
    b) optionally, recovering the β-santalene produced in a).

12. The method of claim 11, further comprising processing the β-santalene to a β-santalene derivative using a chemical or biochemical synthesis or a combination of both.

13. The method of claim 12, wherein the derivative comprises β-santalol.

14. The non-human organism or cell of claim 8, wherein the non-human organism or cell is capable of producing farnesyl pyrophosphate (FPP).

15. A method for producing β-santalene comprising
   a) cultivating the non-human organism or cell of claim 14 under conditions conducive to the production of β-santalene; and
   b) optionally, recovering the β-santalene produced in a).

16. The method of claim 15, further comprising processing the β-santalene to a β-santalene derivative using a chemical or biochemical synthesis or a combination of both.

17. The method of claim 16, wherein the derivative comprises β-santalol.

18. The expression vector of claim 2, wherein the nucleic acid of b) comprises a nucleotide sequence at least 90% identical to SEQ ID NO: 2, SEQ ID NO: 4, SEQ ID NO: 14, SEQ ID NO: 26, wherein the nucleic acid encodes a polypeptide having a β-santalene synthase activity.

19. The non-human host organism or cell of claim 3, the nucleic acid of ii) comprising a nucleotide sequence having at least 90% sequence identity to SEQ ID NO: 2, SEQ ID NO: 4, SEQ ID NO: 14, SEQ ID NO: 26, wherein the nucleic acid encodes a polypeptide having a β-santalene synthase activity.

* * * * *